(12) United States Patent
Darlington et al.

(10) Patent No.: US 9,770,605 B2
(45) Date of Patent: *Sep. 26, 2017

(54) SYSTEM FOR TREATING A VOLUME OF TISSUE WITH HIGH INTENSITY FOCUSED ULTRASOUND

(71) Applicant: Mirabilis Medica, Inc., Bothell, WA (US)

(72) Inventors: Gregory P. Darlington, Snohomish, WA (US); Michael J. Connolly, Bothell, WA (US); Justin A. Reed, Seattle, WA (US); Jessica E. Parsons, Kirkland, WA (US); Roland Horth, Newburyport, MA (US); John Murkowski, Seattle, WA (US); Charles D. Emery, Sammamish, WA (US)

(73) Assignee: Mirabilis Medica, Inc., Bothell, WA (US)

( * ) Notice: Subject to any disclaimer, the term of this patent is extended or adjusted under 35 U.S.C. 154(b) by 198 days.

This patent is subject to a terminal disclaimer.

(21) Appl. No.: 14/733,372

(22) Filed: Jun. 8, 2015

(65) Prior Publication Data

US 2015/0273246 A1    Oct. 1, 2015

Related U.S. Application Data

(63) Continuation of application No. 12/753,813, filed on Apr. 2, 2010, now Pat. No. 9,050,449, which is a
(Continued)

(51) Int. Cl.
*A61H 1/00* (2006.01)
*A61H 1/02* (2006.01)
(Continued)

(52) U.S. Cl.
CPC ...... *A61N 7/02* (2013.01); *A61B 2017/00172* (2013.01); *A61B 2090/378* (2016.02);
(Continued)

(58) Field of Classification Search
None
See application file for complete search history.

(56) References Cited

U.S. PATENT DOCUMENTS 3,470,868 A     10/1969   Krause et al.
3,480,002 A     11/1969   Flaherty et al.
(Continued)

FOREIGN PATENT DOCUMENTS

EP        0 301 360 B1    11/1993
EP        0 614 651 A1     9/1994
(Continued)

OTHER PUBLICATIONS

Cain et al., "Concentric-Ring and Sector-Vortex Phased-Array Applicators for Ultrasound Hyperthermia," *IEEE Transactions on Microwave Theory and Techniques* 34(5):542-551, May 1986.
(Continued)

*Primary Examiner* — James Kish
(74) *Attorney, Agent, or Firm* — Seed IP Law Group LLP

(57) ABSTRACT

A method and system for treating a desired volume of tissue using HIFU or other energy modality includes ablating a pattern of elemental treatment volumes each having a volume that is greater than that of the focal zone of the HIFU transducer but smaller than the overall volume of the desired treatment volume. In at least one embodiment, the elemental treatment volumes are arranged to form a shell which partially or wholly encapsulates the desired volume of tissue, which then necroses in situ. The elemental treatment volumes are created by distributing HIFU energy in multiple doses with repeated passes of the focal zone of the HIFU
(Continued)

transducer in a trajectory over or along a perimeter of each elemental treatment volume.

20 Claims, 22 Drawing Sheets

Related U.S. Application Data continuation-in-part of application No. 12/573,840, filed on Oct. 5, 2009, now Pat. No. 8,845,559.

(60) Provisional application No. 61/102,804, filed on Oct. 3, 2008.

(51) Int. Cl.
*A61H 5/00* (2006.01)
*A61N 7/02* (2006.01)
*A61B 17/00* (2006.01)
*A61N 7/00* (2006.01)
*A61B 90/00* (2016.01)

(52) U.S. Cl.
CPC ............... *A61N 2007/0065* (2013.01); *A61N 2007/0082* (2013.01); *A61N 2007/0091* (2013.01); *A61N 2007/0095* (2013.01)

(56) References Cited

U.S. PATENT DOCUMENTS

| | | |
|---|---|---|
| 3,676,584 A | 7/1972 | Plakas et al. |
| 3,941,112 A | 3/1976 | Habert |
| 4,059,098 A | 11/1977 | Murdock |
| 4,097,835 A | 6/1978 | Green |
| 4,185,502 A | 1/1980 | Frank |
| 4,282,755 A | 8/1981 | Gardineer et al. |
| 4,347,850 A | 9/1982 | Kelly-Fry et al. |
| 4,484,569 A | 11/1984 | Driller et al. |
| 4,665,913 A | 5/1987 | L'Esperance, Jr. |
| 4,742,829 A | 5/1988 | Law et al. |
| 4,756,313 A | 7/1988 | Terwilliger |
| 4,835,689 A | 5/1989 | O'Donnell |
| 4,858,613 A | 8/1989 | Fry et al. |
| 4,865,042 A | 9/1989 | Umemura et al. |
| 4,893,624 A | 1/1990 | Lele |
| 4,938,217 A | 7/1990 | Lele |
| 5,005,579 A | 4/1991 | Wurster et al. |
| 5,036,855 A | 8/1991 | Fry et al. |
| 5,050,610 A | 9/1991 | Oaks et al. |
| 5,080,101 A | 1/1992 | Dory |
| 5,080,102 A | 1/1992 | Dory |
| 5,080,660 A | 1/1992 | Buelna |
| 5,117,832 A | 6/1992 | Sanghvi et al. |
| 5,234,429 A | 8/1993 | Goldhaber |
| 5,271,402 A | 12/1993 | Yeung et al. |
| 5,391,140 A | 2/1995 | Schaetzle et al. |
| 5,441,499 A | 8/1995 | Fritzsch |
| 5,471,988 A | 12/1995 | Fujio et al. |
| 5,474,071 A | 12/1995 | Chapelon et al. |
| 5,492,126 A | 2/1996 | Hennige et al. |
| 5,520,188 A | 5/1996 | Hennige et al. |
| 5,558,092 A | 9/1996 | Unger et al. |
| 5,619,999 A | 4/1997 | Von Behren et al. |
| 5,665,054 A | 9/1997 | Dory |
| 5,666,954 A | 9/1997 | Chapelon et al. |
| 5,676,692 A | 10/1997 | Sanghvi et al. |
| 5,720,287 A | 2/1998 | Chapelon et al. |
| 5,762,066 A | 6/1998 | Law et al. |
| 5,769,790 A | 6/1998 | Watkins et al. |
| 5,810,007 A | 9/1998 | Holupka et al. |
| 5,882,302 A | 3/1999 | Driscoll, Jr. et al. |
| 5,976,092 A | 11/1999 | Chinn |
| 5,993,389 A | 11/1999 | Driscoll, Jr. et al. |
| 6,002,251 A | 12/1999 | Sun |
| 6,007,499 A | 12/1999 | Martin et al. |
| 6,042,556 A | 3/2000 | Beach et al. |
| 6,050,943 A | 4/2000 | Slayton et al. |
| 6,068,653 A | 5/2000 | LaFontaine |
| 6,071,239 A | 6/2000 | Cribbs et al. |
| 6,083,159 A | 7/2000 | Driscoll, Jr. et al. |
| 6,126,607 A | 10/2000 | Whitmore, III et al. |
| 6,128,522 A | 10/2000 | Acker et al. |
| 6,196,972 B1 | 3/2001 | Moehring |
| 6,217,530 B1 | 4/2001 | Martin et al. |
| 6,254,601 B1 | 7/2001 | Burbank et al. |
| 6,267,734 B1 | 7/2001 | Ishibashi et al. |
| 6,315,741 B1 | 11/2001 | Martin et al. |
| 6,361,531 B1 | 3/2002 | Hissong |
| 6,390,973 B1 | 5/2002 | Ouchi |
| 6,425,867 B1 | 7/2002 | Vaezy et al. |
| 6,432,067 B1 | 8/2002 | Martin et al. |
| 6,451,013 B1 | 9/2002 | Bays et al. |
| 6,461,314 B1 | 10/2002 | Pant et al. |
| 6,488,639 B1 | 12/2002 | Ribault et al. |
| 6,500,133 B2 | 12/2002 | Martin et al. |
| 6,508,774 B1 | 1/2003 | Acker et al. |
| 6,537,224 B2 | 3/2003 | Mauchamp et al. |
| 6,602,251 B2 | 8/2003 | Burbank et al. |
| 6,613,004 B1 | 9/2003 | Vitek et al. |
| 6,618,620 B1 | 9/2003 | Freundlich et al. |
| 6,626,855 B1 | 9/2003 | Weng et al. |
| 6,633,658 B1 | 10/2003 | Dabney et al. |
| 6,645,162 B2 | 11/2003 | Friedman et al. |
| 6,666,835 B2 | 12/2003 | Martin et al. |
| 6,676,601 B1 | 1/2004 | Lacoste et al. |
| 6,692,450 B1 | 2/2004 | Coleman |
| 6,716,184 B2 | 4/2004 | Vaezy et al. |
| 6,719,694 B2 | 4/2004 | Weng et al. |
| 6,740,082 B2 | 5/2004 | Shadduck |
| 6,764,488 B1 | 7/2004 | Burbank et al. |
| 6,840,936 B2 | 1/2005 | Sliwa, Jr. et al. |
| 6,936,046 B2 | 8/2005 | Hissong et al. |
| 7,063,666 B2 | 6/2006 | Weng et al. |
| 7,090,643 B2 | 8/2006 | Fidel et al. |
| 7,105,007 B2 | 9/2006 | Hibler |
| 7,175,596 B2 | 2/2007 | Vitek et al. |
| 7,258,674 B2 | 8/2007 | Cribbs et al. |
| 7,399,284 B2 | 7/2008 | Miwa et al. |
| 7,452,357 B2 | 11/2008 | Vlegele et al. |
| 7,470,241 B2 | 12/2008 | Weng et al. |
| 7,473,224 B2 | 1/2009 | Makin |
| 7,699,780 B2 | 4/2010 | Vitek et al. |
| 7,699,782 B2 | 4/2010 | Angelsen et al. |
| 7,722,539 B2 | 5/2010 | Carter et al. |
| 7,914,452 B2 | 3/2011 | Hartley et al. |
| 7,993,289 B2 | 8/2011 | Quistgaard et al. |
| 2001/0012934 A1 | 8/2001 | Chandrasekaran et al. |
| 2002/0029036 A1 | 3/2002 | Goble et al. |
| 2002/0065512 A1 | 5/2002 | Fjield et al. |
| 2002/0120259 A1 | 8/2002 | Lettice et al. |
| 2003/0004439 A1 | 1/2003 | Pant et al. |
| 2003/0060736 A1 | 3/2003 | Martin et al. |
| 2003/0135135 A1 | 7/2003 | Miwa et al. |
| 2003/0149380 A1 | 8/2003 | Fujimoto et al. |
| 2003/0233045 A1 | 12/2003 | Vaezy et al. |
| 2004/0030268 A1 | 2/2004 | Weng et al. |
| 2004/0030269 A1 | 2/2004 | Horn et al. |
| 2004/0039312 A1 | 2/2004 | Hillstead et al. |
| 2004/0082859 A1 | 4/2004 | Schaer |
| 2004/0152986 A1 | 8/2004 | Fidel et al. |
| 2004/0153126 A1 | 8/2004 | Okai |
| 2004/0242999 A1 | 12/2004 | Vitek et al. |
| 2004/0243112 A1 | 12/2004 | Bendett et al. |
| 2004/0243201 A1 | 12/2004 | Goldman et al. |
| 2005/0000097 A2 | 1/2005 | Bednar et al. |
| 2005/0038340 A1 | 2/2005 | Vaezy et al. |
| 2005/0085726 A1 | 4/2005 | Lacoste et al. |
| 2005/0101854 A1 | 5/2005 | Larson et al. |
| 2005/0154431 A1 | 7/2005 | Quistgaard et al. |
| 2005/0203399 A1 | 9/2005 | Vaezy et al. |
| 2005/0256405 A1 | 11/2005 | Makin et al. |
| 2005/0267454 A1 | 12/2005 | Hissong et al. |
| 2006/0052701 A1 | 3/2006 | Carter et al. |
| 2006/0058671 A1 | 3/2006 | Vitek et al. |

(56) References Cited

U.S. PATENT DOCUMENTS

| | | |
|---|---|---|
| 2006/0122509 A1 | 6/2006 | Desilets |
| 2006/0264748 A1 | 11/2006 | Vaezy et al. |
| 2007/0010805 A1 | 1/2007 | Fedewa et al. |
| 2007/0016039 A1 | 1/2007 | Vortman et al. |
| 2007/0066990 A1 | 3/2007 | Marsella et al. |
| 2007/0194658 A1 | 8/2007 | Zhang et al. |
| 2007/0197918 A1 | 8/2007 | Vitek et al. |
| 2007/0238994 A1 | 10/2007 | Stecco et al. |
| 2007/0255267 A1 | 11/2007 | Diederich et al. |
| 2008/0033419 A1 | 2/2008 | Nields et al. |
| 2008/0039724 A1 | 2/2008 | Seip et al. |
| 2008/0058683 A1 | 3/2008 | Gifford et al. |
| 2008/0071165 A1 | 3/2008 | Makin et al. |
| 2008/0086036 A1 | 4/2008 | Hartley et al. |
| 2008/0114274 A1 | 5/2008 | Moonen et al. |
| 2008/0125771 A1 | 5/2008 | Lau et al. |
| 2008/0221647 A1 | 9/2008 | Chamberland et al. |
| 2008/0281314 A1 | 11/2008 | Johnson et al. |
| 2008/0312561 A1 | 12/2008 | Chauhan |
| 2008/0319436 A1 | 12/2008 | Daniel et al. |
| 2009/0036774 A1 | 2/2009 | Weng et al. |
| 2009/0069677 A1 | 3/2009 | Chen et al. |
| 2009/0228001 A1 | 9/2009 | Pacey |
| 2009/0281463 A1 | 11/2009 | Chapelon et al. |
| 2009/0326420 A1 | 12/2009 | Moonen et al. |
| 2010/0036292 A1 | 2/2010 | Darlington et al. |
| 2010/0241005 A1 | 9/2010 | Darlington et al. |

FOREIGN PATENT DOCUMENTS

| | | |
|---|---|---|
| EP | 0 734 742 A2 | 10/1996 |
| EP | 1 726 267 A2 | 11/2006 |
| JP | 5-23336 A | 2/1993 |
| JP | 2000-237205 A | 9/2000 |
| JP | 2002-536040 A | 10/2002 |
| JP | 2004-534582 A | 11/2004 |
| JP | 2009-541000 A | 11/2009 |
| JP | 2011-530343 A | 12/2011 |
| WO | 93/17646 A2 | 9/1993 |
| WO | 94/27502 A1 | 12/1994 |
| WO | 95/20360 A1 | 8/1995 |
| WO | 97/00646 A1 | 1/1997 |
| WO | 97/10768 A2 | 3/1997 |
| WO | 00/45706 A1 | 8/2000 |
| WO | 01/71380 A2 | 9/2001 |
| WO | 02/100486 A1 | 12/2002 |
| WO | 03/002189 A2 | 1/2003 |
| WO | 2004/073524 A1 | 9/2004 |
| WO | 2005/000097 A2 | 1/2005 |
| WO | 2006/097661 A1 | 9/2006 |
| WO | 2008/003910 A1 | 1/2008 |
| WO | 2010/017419 A2 | 2/2010 |
| WO | 2010/040140 A2 | 4/2010 |

OTHER PUBLICATIONS

Chapelon et al., "The Feasibility of Tissue Ablation Using High Intensity Electronically Focused Ultrasound," Proceedings of the IEEE Ultrasonics Symposium, Baltimore, Oct. 31-Nov. 3, 1993, pp. 1211-1214.

Chen et al., "Effect of Blood Perfusion on the Ablation of Liver Parenchyma With High-Intensity Focused Ultrasound," *Physics in Medicine and Biology* 38(11):1661-1673, Nov. 1993.

Cheng et al., "High-Intensity Focused Ultrasound in the Treatment of Experimental Liver Tumour," *Journal of Cancer Research and Clinical Oncology* 123(4):219-223, Apr. 1997.

Coad, "Thermal Fixation: A Central Outcome of Hyperthermic Therapies," Proceedings of the SPIE Conference on Thermal Treatment of Tissue: Energy Delivery and Assessment III 5698:15-22, San Jose, Calif., Jan. 23, 2005.

Daum et al., "A 256-Element Ultrasonic Phased Array System for the Treatment of Large Volumes of Deep Seated Tissue," *IEEE Transactions on Ultrasonics, Ferroelectrics, and Frequency Control* 46(5):1254-1268, Sep. 1999.

Delon-Martin et al., "Venous Thrombosis Generation by Means of High-Intensity Focused Ultrasound," *Ultrasound in Medicine & Biology* 21(1):113-119, 1995.

Enholm et al., "Improved Volumetric MR-HIFU Ablation by Robust Binary Feedback Control," *IEEE Transactions on Biomedical Engineering* 57(1):103-113, Jan. 2010.

Friedland, "Ultrasonic Therapy," *American Journal of Nursing* 59(9):1272-1275, Sep. 1959.

Fry, "Recent Bioeffects With Ultrasound on the Reproductive System and Solid Tumors," *Journal of the Acoustical Society of America* 63(Suppl. 1):S13, May 1978.

Hallberg et al., "Menstrual Blood Loss—A Population Study: Variation at Different Ages and Attempts to Define Normality," *Acta Obstetricia et Gynecologica Scandinavica* 45(3):320-351, 1966.

Lee et al., "Comparison of Wet Radiofrequency Ablation With Dry Radiofrequency Ablation and Radiofrequency Ablation Using Hypertonic Saline Preinjection: Ex Vivo Bovine Liver," *Korean Journal of Radiology* 5(4):258-265, Dec. 2004.

Lee et al., "Wet Radio-Frequency Ablation Using Multiple Electrodes: Comparative Study of Bipolar Versus Monopolar Modes in the Bovine Liver," *European Journal of Radiology* 54:408-417, Jun. 2005.

Lui et al., "Nonlinear Absorption in Biological Tissue for High Intensity Focused Ultrasound," *Ultrasonics* 44:e27-e30, 2006.

Mittleman et al., "Use of the Saline Infusion Electrode Catheter for Improved Energy Delivery and Increased Lesion Size in Radiofrequency Catheter Ablation," *Pacing and Clinical Electrophysiology* 18(5 Pt. 1):953-1081, May 1995.

Mougenot et al., "Automatic Spatial and Temporal Temperature Control for MR-Guided Focused Ultrasound Using Fast 3D MR Thermometry and Multispiral Trajectory of the Focal Point," *Magnetic Resonance in Medicine* 52:1005-1015, 2004.

Mougenot et al., "Three-Dimensional Spatial and Temporal Temperature Control with MR Thermometry-Guided Focused Ultrasound (MRgHIFU)," *Magnetic Resonance in Medicine* 61:603-617, 2009.

Ngo et al., "An Experimental Analysis of a Sector-Vortex Phased Array Prototype," *Ultrasonics Symposium Proceedings*, 1989, pp. 999-1002.

Orsini-Meinhard, "UW Tech-Transfer Program Putting Discoveries to Work," The Seattle Times, May 27, 2007, 8 pages.

Rabkin, "Biological and Physical Mechanisms of HIFU-Induced Hyperecho in Ultrasound Images," *Ultrasound in Medicine & Biology* 32(11):1721-1729, Nov. 2006.

Rabkin et al., "Hyperecho in Ultrasound Images of HIFU Therapy: Involvement of Cavitation," *Ultrasound in Medicine and Biology* 31(7):947-956, Jul. 2005.

Salomir et al., "Local Hyperthermia With MR-Guided Focused Ultrasound: Spiral Trajectory of the Focal Point Optimized for Temperature Uniformity in the Target Region," *Journal of Magnetic Resonance Imaging* 12(4):571-583, Oct. 1, 2000.

Sanghvi, "High Intensity Focused Ultrasound (HIFU) for the Treatment of Rectal Tumors: A Feasibility Study," *Proceedings of IEEE Ultrasonics Symposium* 3:1895-1898, Cannes, France, Nov. 1-4, 1994.

"ThermoDox™ Animal Studies to Be Presented at 6th International Symposium on Therapeutic Ultrasound in Oxford, England," Aug. 30-Sep. 2, 2006, Celsion, Inc., http://www.celsion.com/news/releasedetail.dfm, retrieved Oct. 8, 2007, 2 pages.

"ThermoDox™: Heat-Activated Liposome Drug," © 2007 Celsion, Inc., http://www.celsion.com/products/ThermoDox.cfm, retrieved Oct. 8, 2007, 3 pages.

Umemura et al., "Acoustical Evaluation of a Prototype Sector-Vortex Phased-Array Applicator," *IEEE Transactions on Ultrasonics, Ferroelectrics, and Frequency Control* 39(1):32-38, Jan. 1992.

Vaezy et al., "Image-Guided Acoustic Therapy," *Annual Review of Biomedical Engineering* 3:375-390, Aug. 2001.

Winter et al., "Focal Tumor Ablation: A New Era in Cancer Therapy," *Ultrasound Quarterly* 22(3):204-209, Sep. 2006.

Zanelli et al., "Design and Characterization of a 10 cm Annular Array Transducer for High Intensity Focused Ultrasound (HIFU)

(56) References Cited

OTHER PUBLICATIONS

Applications," *Proceedings of the IEEE Ultrasonics Symposium* 3:1887-1890, Cannes, France, Nov. 1-4, 1994.

European Search Report mailed Oct. 15, 2012, in European Application No. 09 81 8624, filled Oct. 5, 2009, 7 pages.

Extended European Search Report mailed Feb. 26, 2010, issued in corresponding European Patent Application No. 07811847.8, filed Apr. 13, 2007, 7 pages.

Extended European Search Report mailed Nov. 27, 2014, issued in European Application No. EP 11763567.2, filed Apr. 4, 2011, 7 pages.

First Office Action mailed Nov. 4, 2014, issued in Chinese Application No. CN 201180027496.6, filed Apr. 4, 2011, 7 pages.

International Search Report and Written Opinion mailed Jun. 26, 2009, issued in corresponding International Application No. PCT/US2008/082829, filed Jul. 11, 2008, 15 pages.

International Search Report and Written Opinion mailed May 11, 2010, issued in corresponding International Application No. PCT/US2009/059589, filed Oct. 5, 2009, 10 pages.

International Search Report and Written Opinion mailed May 18, 2010, issued in corresponding International Application No. PCT/US2009/053050, filed Aug. 6, 2009, 15 pages.

International Search Report and Written Opinion mailed Oct. 26, 2010, issued in corresponding International Application No. PCT/US2010/026565, filed Mar. 8, 2010, 10 pages.

International Search Report and Written Opinion mailed Dec. 27, 2011, issued in corresponding International Application No. PCT/US2011/031129, filed Apr. 4, 2011, 13 pages.

International Search Report and Written Opinion mailed Mar. 15, 2012, issued in corresponding International Application No. PCT/US2011/048331, filed Aug. 18, 2011, 8 pages.

Japanese Office Action Notice of Reasons for Rejection dated Nov. 15, 2013, issued in Japanese Patent Application No. 2011-530293, filed Oct. 5, 2009, 5 pages.

Japanese Office Action Notice of Grounds for Rejection dated Jan. 6, 2015, issued in Japanese Patent Application No. 2013-502919, filed Apr. 4, 2011, 2 pages.

Notice of Reasons for Rejection mailed Mar. 12, 2012, issued in corresponding Japanese Patent Application No. 2009-505639, filed Apr. 13, 2007, 7 pages.

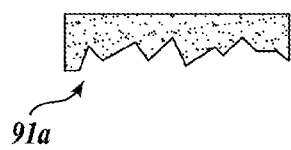
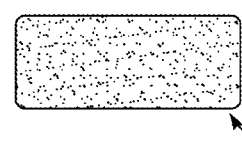
Fig. 3G.   Fig. 3H.
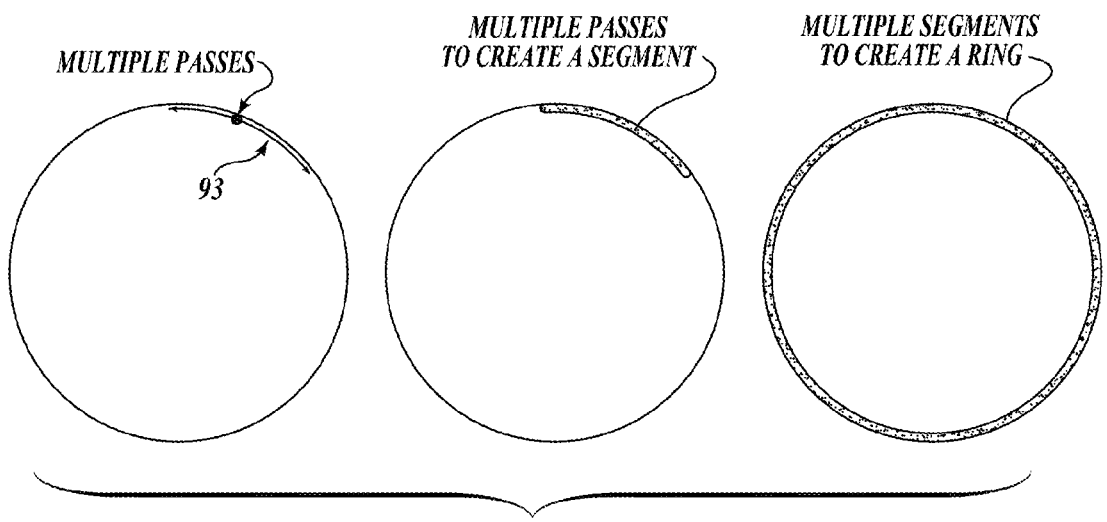
Fig. 3I.

WOBBLE AXIS VARIES OVER THE RANGE OF 'α'
AND RADIUS AXIS VARIES OVER THE RANGE OF 'r'
TO CREATE UNIT VOLUME

*x* AND *y* VARY TO CREATE A UNIT VOLUME

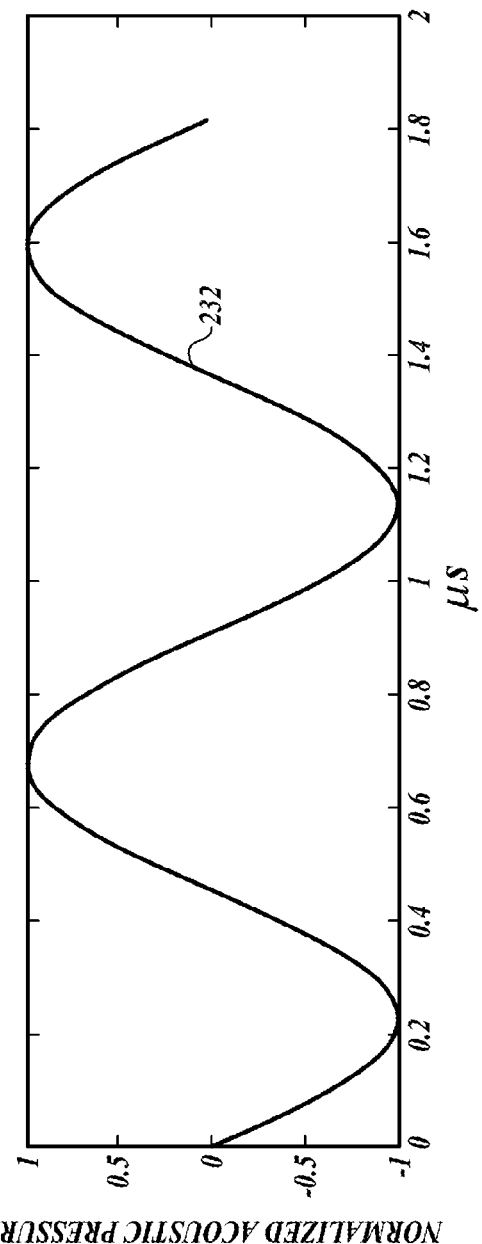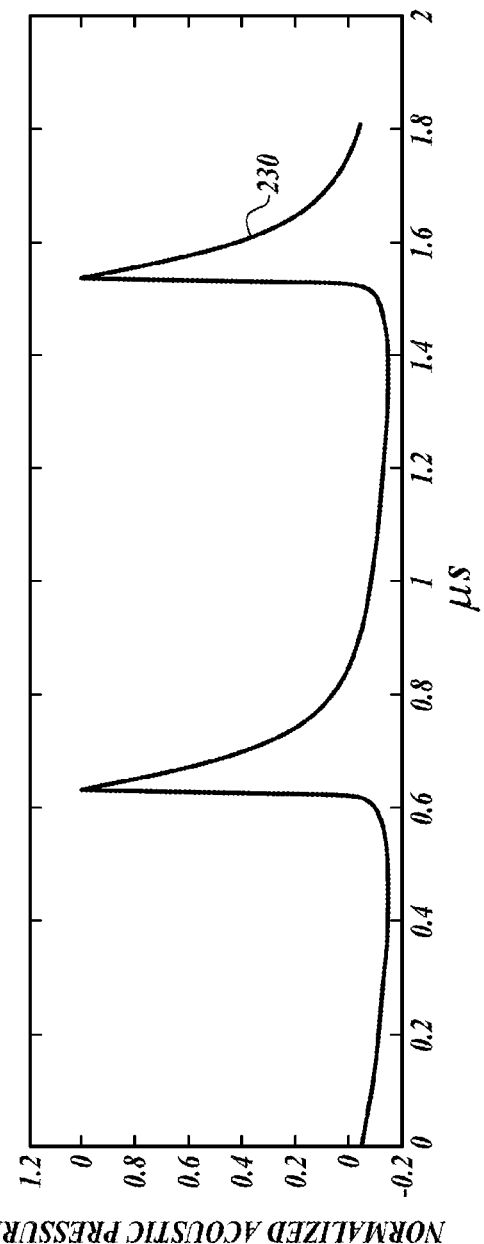

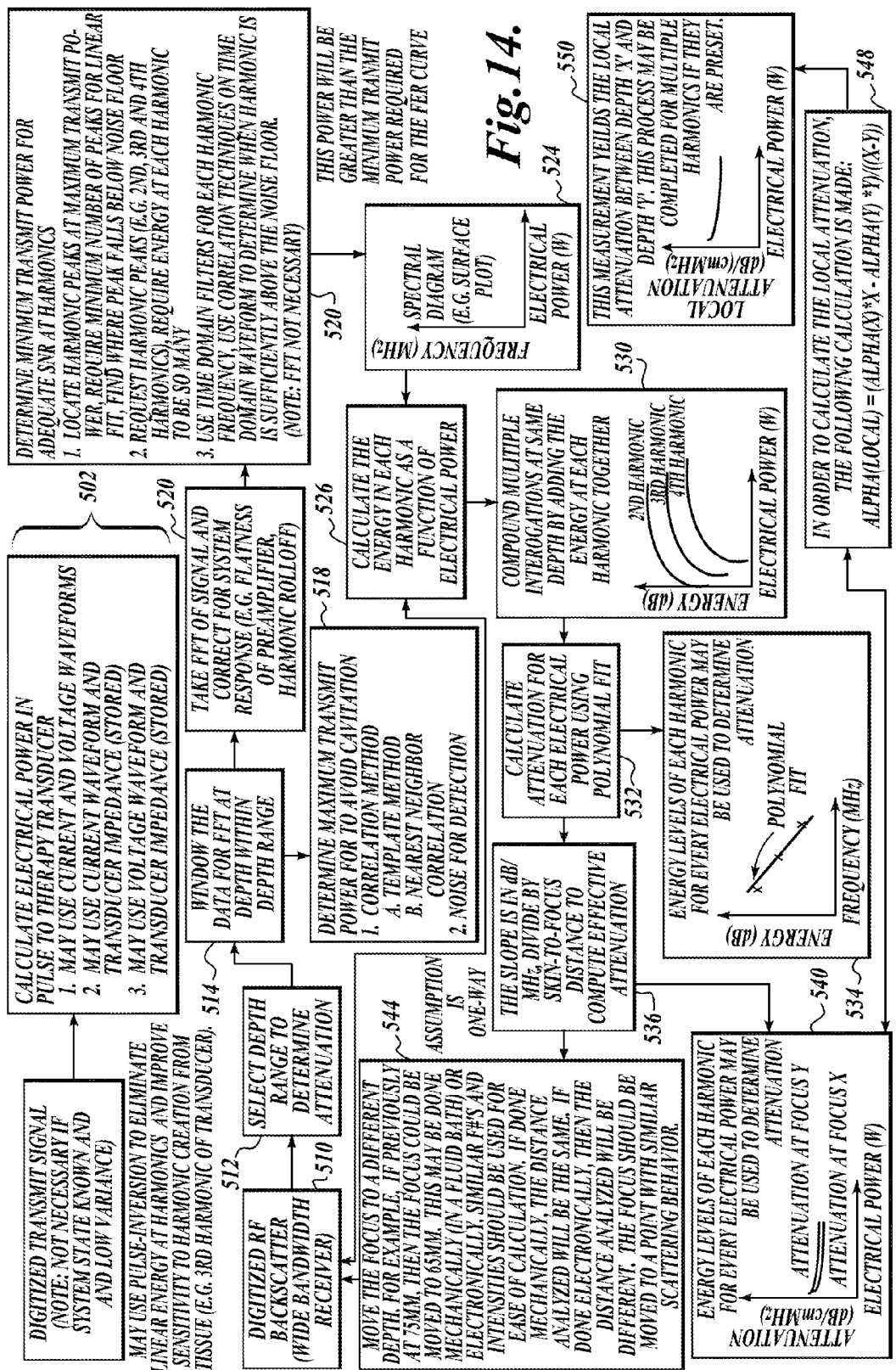

SYSTEM FOR TREATING A VOLUME OF TISSUE WITH HIGH INTENSITY FOCUSED ULTRASOUND

BACKGROUND

Technical Field

The technology disclosed herein relates to methods and apparatus for the treatment of internal body tissues and in particular to the treatment of internal body tissues with high intensity focused ultrasound (HIFU).

Description of the Related Art

There are numerous techniques that are currently used for the treatment of internal body tissues. For example, internal cancerous and non-cancerous tumors can be treated with a variety of techniques such as surgery, radiation and chemotherapy. Each of these techniques offers advantages and disadvantages. One promising non-invasive technology for treating internal body tissues is high intensity focused ultrasound (HIFU). With HIFU, high intensity ultrasound energy is focused at a desired treatment volume. The energy causes tissue destruction via both thermal and mechanical mechanisms.

One of the drawbacks of using HIFU to treat internal body tissues is the time required to treat a given volume of tissue. Currently proposed HIFU procedures may take up to 3 hours to treat a single tumor, which has contributed to poor acceptance of these procedures by both physicians and patients. In addition, the amount of energy required to completely ablate a large volume of tissue results in substantial thermal conduction outward from the ablation volume, which can raise the risk of thermal damage to surrounding healthy tissue.

Given these problems, there is a need for a method of treating internal body tissues in a manner that reduces treatment time, while improving safety, effectiveness and ease of use, and reducing total required energy deposition.

BRIEF SUMMARY

To address the problems discussed above, the technology disclosed herein relates to a system for treating uterine fibroids or other tissue that is compact enough to be used in a physician's office. The system treats the tissue with energy from an energy source, which may include high intensity focused ultrasound (HIFU). Such energy sources could also include radiofrequency, radiation, microwave, cryotherapy, laser, etc. However the preferred embodiment is HIFU, due to its unique ability to be non-invasively focused deep inside body tissues without the need for punctures or incisions.

In one embodiment, a desired target volume of tissue is treated with HIFU by ablating a number of adjacent elemental treatment volumes to form "building blocks" used to treat the full target volume of tissue. Each elemental treatment volume is created by directing the focal zone of a HIFU transducer to ablate a sub-volume that is larger than the focal zone itself but smaller than the overall desired treatment volume. Each elemental treatment volume is created by repeatedly directing the focal zone of the HIFU transducer over the perimeter of the elemental treatment volume as treatment energy is being applied. Treatment signals from the HIFU transducer can be applied to the tissue without using temperature data or feedback control even in the presence of bubbles such that the treatment time is significantly decreased.

In one embodiment, a mechanical or electronic steering apparatus directs the focal zone of a HIFU beam around the perimeter of the elemental treatment volume until the tissue encompassed by the perimeter is ablated. In one embodiment, a center region of the elemental treatment volume is not directly ablated but is treated by thermal conduction as the perimeter is ablated.

In one embodiment, the disclosed technology includes a HIFU transducer that is configured to deliver treatment energy to a focal zone and a computer controlled beam steerer for repeatedly positioning the focal zone over a perimeter of an elemental treatment volume as treatment energy is applied.

In one embodiment, a pattern of elemental treatment volumes is created to form a shell of ablated tissue surrounding the treatment volume (similar to the geometry of an eggshell surrounding an egg). Treating a desired tissue volume using this type of shell ablation has two primary utilities in HIFU therapy: (1) In one embodiment, the ablated shell interrupts the supply of blood to the interior of the treatment volume, causing the otherwise untreated tissue located within the shell to ischemically necrose in situ. In this manner, the ischemic damage to the center of the volume results in the destruction of the entire volume over time, even though only the outer boundary is directly treated with HIFU. (2) In another embodiment, the elemental treatment volumes comprising the shell pattern are deposited in such a way that heat conduction toward the interior of the volume results in immediate thermal destruction of the inner tissue, even though only the outer boundary is directly ablated with HIFU energy. Both of these utilities provided by shell ablation serve to significantly improve the efficiency of HIFU therapy because they result in an effective tissue treatment volume that is larger than the volume directly ablated with HIFU energy. Leveraging either or both of these shell ablation advantages increases the throughput achieved by a given HIFU procedure.

In another embodiment, a number of elemental treatment volumes are created to fill or partially fill the target treatment volume. With this technique, a greater percentage of tissue within the treatment volume is directly necrosed by exposure to the ablating energy than is the case when only the outer boundary is ablated.

In another embodiment, a HIFU treatment device directs a focal zone of a HIFU transducer to move in a path to surround or envelop a tissue volume. The pattern in which the focal zone of the HIFU transducer is moved results in creating a series of ablated tissue toroids of varying diameter that are stacked to surround and envelop the tissue volume. In yet another embodiment, the focal zone is moved to create a spiral shell of ablated tissue to envelop the treatment volume.

In order to minimize treatment time and required user skill, one embodiment employs a computer-controlled mechanism to automatically move the HIFU focal zone and apply HIFU energy in such a manner to create the desired elemental treatment volume and/or geometric shell while the user simply holds the applicator stationary.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

BRIEF DESCRIPTION OF THE SEVERAL VIEWS OF THE DRAWINGS

The foregoing aspects and many of the attendant advantages of this technology will become more readily appreciated by reference to the following detailed description, when taken in conjunction with the accompanying drawings, wherein:

FIG. 3G illustrates the uneven profile of treated tissue created by the application of energy in a single pass of the HIFU focus along the tissue volume;

FIG. 3H illustrates the more even profile of treated tissue created by the application of energy in multiple passes of the HIFU focus along the tissue volume;

FIG. 3I illustrates creating an arc or segment elemental treatment volume by directing a focal zone back and forth over a portion of the perimeter of the total treatment volume desired;

FIGS. 8A and 8B illustrate two different HIFU signal waveforms;

FIG. 14 is a flow diagram of a method of estimating the attenuation of a HIFU signal at a focal zone of a HIFU transmitter versus changes in input power.

DETAILED DESCRIPTION

As indicated above, the technology disclosed herein relates to a method of treating internal body tissues such as uterine fibroids, benign or malignant tumors, or the like. Although the following description is directed to the use of the technology to treat uterine fibroids, it will be appreciated by those of skill in the art that the technology can be used to treat a volume of any internal body tissue. In one embodiment, the desired treatment volume is treated by creating a pattern of one or more elemental treatment volumes in the tissue. Though the technology disclosed herein describes several possible geometries for these elemental treatment volumes, each type of elemental volume shares the common feature that it is comprised of a volume of ablated tissue that is greater than the volume of the HIFU focal zone due to controlled motion of that focal zone around or along the elemental volume in a prescribed manner. The acoustic focal zone referenced herein is commonly defined as the volume encompassed by the −6 dB pressure contour of the acoustic waveform as measured from its spatial maximum. Those skilled in the art will recognize that the dimensions of this −6 dB pressure contour are also referred to as the full-width half-maximum, or FWHM, dimensions. A typical focal zone as implemented in the embodiments described herein is ovoid in shape, with FWHM dimensions of approximately 10 mm. in length along the beam axis and 2 mm. in width perpendicular to the beam axis.

In accordance with an embodiment of the disclosed technology, a desired volume of tissue to be treated is exposed to energy that ablates the tissue in a shell-like pattern, which completely or partially surrounds the tissue volume while only directly ablating the outer boundary. The tissue encompassed by the shell then remains in the body and necroses in situ due to effects other than direct ablation. These other effects causing in situ necrosis may include some combination of:

1. ischemic necrosis, resulting from partial or complete isolation of an encapsulated region from a surrounding blood supply;

2. indirect thermal necrosis, resulting from inward thermal conduction occurring during the creation of the ablated shell; and/or 3. secondary injury due to normal healing processes (inflammation, apoptosis, etc.).

The necrosed tissue located inside the ablated shell of the treated volume is subsequently resorbed and/or healed by normal body mechanisms.

Figure 1:
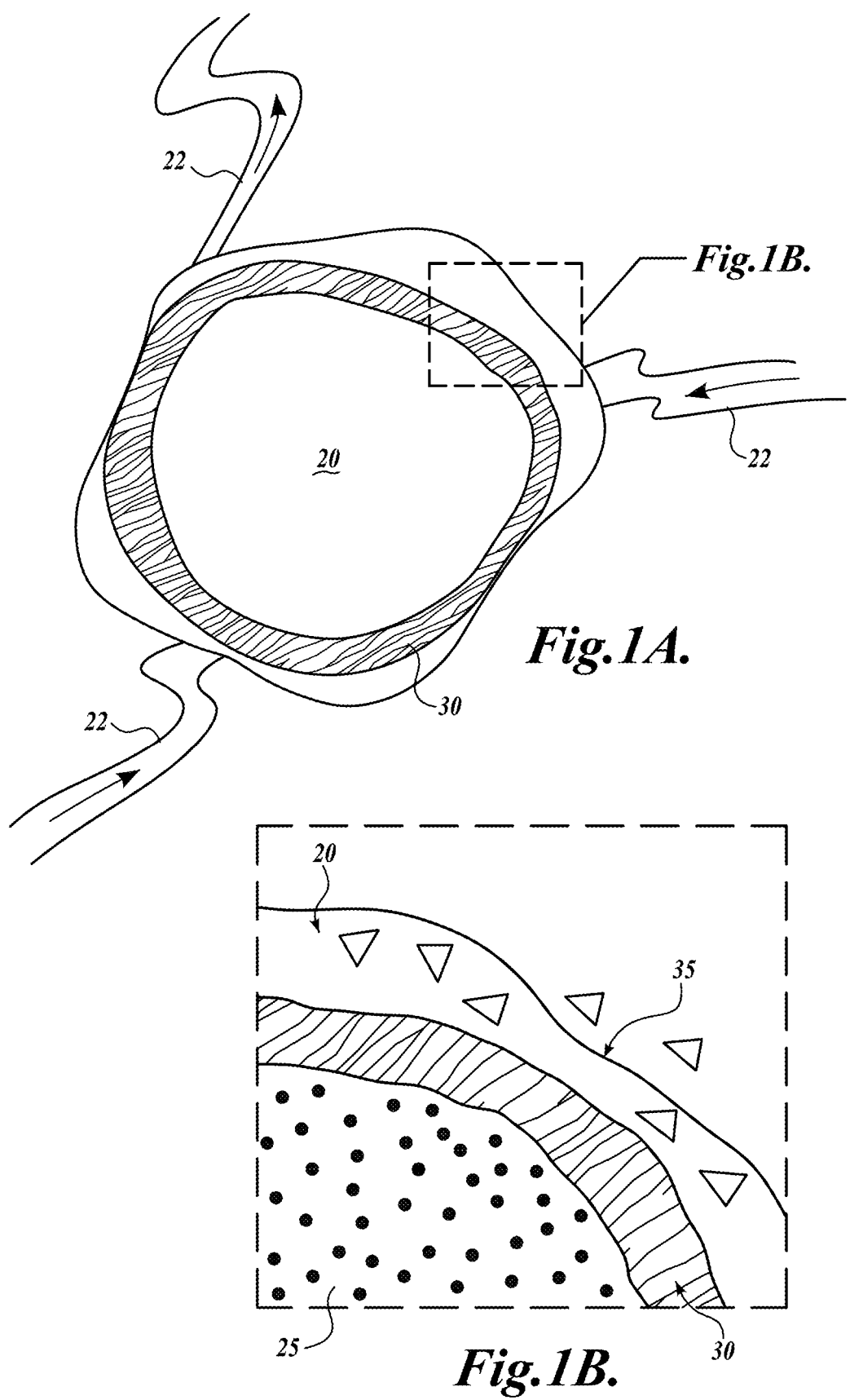
FIG. 1A shows an internal tissue volume to be surrounded with an ablated shell in accordance with one embodiment of the disclosed technology.
FIG. 1B is a detailed view of tissue inside and outside of the ablated shell.

FIG. 1A illustrates a tissue volume, such as a uterine fibroid 20, to be treated. Uterine fibroids may be irregularly shaped but are often generally spherical or oval shaped. The fibroid 20 includes one or more blood vessels 22 that supply the fibroid 20 with blood. In order to treat the fibroid 20, a 3-dimensional ablated shell 30 is formed inside the periphery of the fibroid 20 in a manner that isolates the fibroid tissue inside the shell from the blood vessels 22 that supply blood to, and take blood from the fibroid 20. By cutting off the interior tissue from its blood supply with the ablated shell 30, this interior tissue can be left in the body to ischemically necrose and eventually be absorbed or healed via normal body healing mechanisms over a period of days/weeks.

In one embodiment, an ablated shell 30 is created by exposing the tissue situated in the shell to HIFU energy for a sufficient time or at sufficient power so as to cause direct tissue necrosis. It should be noted that throughout this description, the concepts of applied HIFU power and energy are used to generally describe the amplitude or "strength" of the HIFU signal transmitted into tissue. In this sense, the terms "HIFU power" and "HIFU energy" can generally be used interchangeably, except in those instances where one or the other of these particular quantities is implied by the context in which it is used. This is to be distinguished from secondary ischemic necrosis that occurs in the tissue inside the shell as a result of it being cut off from its blood supply or as a result of other effects listed above. Because the volume of tissue ablated to create the shell is smaller than the overall volume of tissue to be treated, the time required to treat the combined mass of tissue (i.e. shell plus encapsulated volume) is reduced below that which would be required if the entire volume were to be directly ablated. As used herein, the term "ablation" refers to the direct necrosis of tissue resulting from the immediate thermal and/or mechanical effects caused by exposure of the tissue to the energy source. Also as used herein, the term "shell" refers to an ablated surface which reduces or eliminates blood flow across that surface. The geometry of this surface may be such that it entirely encapsulates a volume (e.g., a sphere) or non-closed such that it only partially encapsulates the volume (e.g., a concave disk). The term "encapsulate" refers to creation of such surfaces.

In FIG. 1A, the shell 30 is shown as fitting entirely within volume of the fibroid 20. However, the size of the shell may be varied so that its inner non-ablated region encapsulates the entire fibroid 20. Alternatively, the fibroid 20 may have multiple shells created therein.

In another embodiment, one or more partial shells are created which do not entirely encapsulate the tissue site, but reduce or eliminate blood flow to or from its interior across those partial shell(s). This leads to necrosis of at least part of the tissue volume.

FIG. 1B illustrates a close-up view of the interior of the fibroid 20 and the ablated shell 30 that surrounds it. As indicated above, the fibroid 20 includes an interior region 25 within the ablated shell 30 that will ischemically necrose by virtue of the tissue being cut off from an external blood supply (with some contributions via other secondary injury pathway mechanisms associated with healing, e.g., inflammation, apoptosis, et. al.). Tissue that forms the ablated shell 30 is directly necrosed via thermal and/or mechanical effects of exposure to the focal zone of the HIFU beam. Some fibroid tissue 35 external to the ablated shell 30 may also be partially or completely destroyed via thermal necrosis (due to heat conducted from the ablated shell 30) and/or secondary injury pathway mechanisms (ischemia, inflammation, apoptosis, et. al.).

Figure 2:
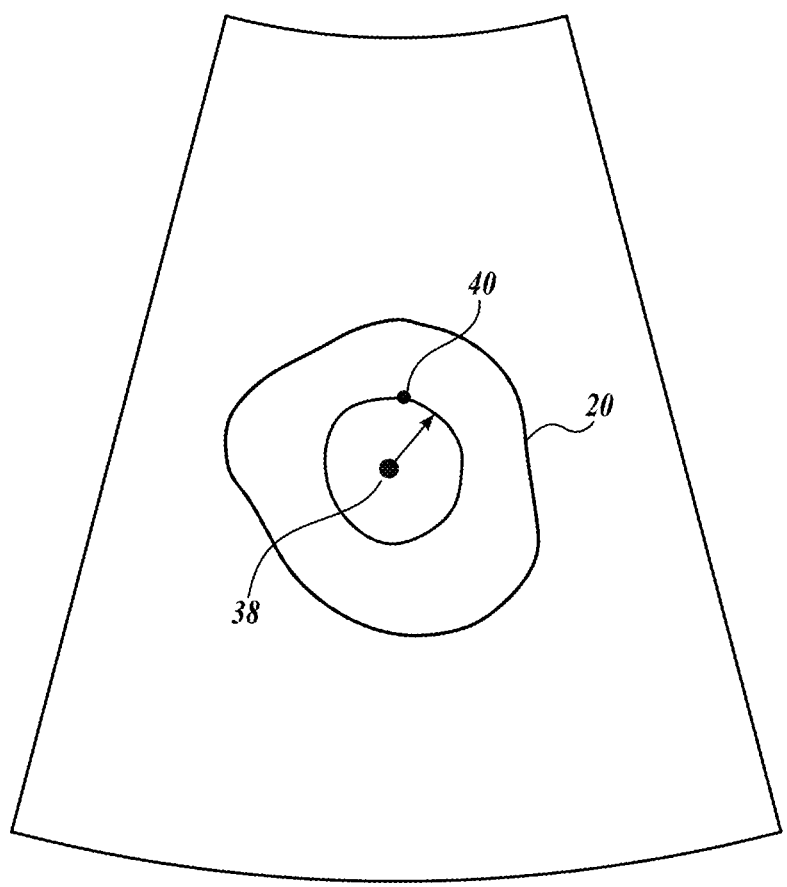
FIG. 2 illustrates an ultrasound image of a uterine fibroid tumor to be treated.

FIG. 2 illustrates a 2-dimensional image of a fibroid 20 produced with an ultrasound imaging transducer and other ultrasound imaging components. As will be explained in further detail below, in one embodiment, an imaging transducer and HIFU transducer are combined as a single unit. In one embodiment, an ultrasound imaging transducer, ultrasound image processor and display (all not shown) are used to produce the image of the fibroid 20 for a physician. The display may include a crosshair or other marker 38 on the image of the fibroid 20 that indicates a reference point with respect to the focal zone of the HIFU transducer so that a user can aim the HIFU transducer at the tissue volume. The physician can interact with the display by, for example, adjusting the radius of a circular marker ring 40 that is centered around the crosshair 38 in order to specify the boundaries of the desired treatment volume or the boundaries of the ablated shell to be created (which may be the same). From the boundaries defined by the size of the marker ring 40, a processing system, such as general or special purpose computer (not shown) computes the size of the ablated shell that should be created to encapsulate the fibroid 20. In some embodiments, the marker ring 40 may be adjustable to form shapes other than a circle, such as ovals or cones, etc., by, for example, stretching the sides of the marker ring 40 in order to allow the physician to define the shape of the three-dimensional ablated shell. In one embodiment, the size of the marker ring 40 is adjusted manually by the physician. In another embodiment, image processing techniques may be used to automatically size the marker ring based on an estimate of the boundaries of the tissue to be treated. The boundaries may be further adjusted by the physician if desired. In some embodiments, the boundaries may be adjusted on a three-dimensional image of the tissue. In another embodiment, an image processing algorithm may automatically detect the edges of the structure to treat (e.g. boundary detection). In this case, the physician may locate the structure to treat by placing one or many point(s) (crosshairs) inside the structure. Next, an image processing algorithm would seek out the boundaries of the structure by (i) identifying local changes in contrast (e.g. speckle brightness) in the ultrasound image (ii) identifying areas of specular backscatter versus backscatter from speckle targets. As one skilled in the art would appreciate, other techniques are possible to identify the boundaries. Once the boundaries have been identified either manually, semi-automatically, or automatically, an automatic treatment planning algorithm may be used to determine the number and position of elemental treatment volumes required to yield a fully ablated shell. The physician could walk through the order of the treatment on the ultrasound image prior to HIFU delivery and make any necessary adjustments. Once the size of the shell to be created is determined and/or order determined, a computer with the HIFU treatment system begins controlling the position of the focal zone of the HIFU transducer to ablate the tissue to create the shell.

In another embodiment, the target volume may be larger than the ultrasound image available. Another possibility that may be encountered is that the range of movement of the therapy beam does not allow the entire target to be treated. In the first case, multiple ultrasound 2D images or 3D volumes may be stitched together to visualize the full extent of the target by manually moving the applicator. This image data may be stored for future reference. Next, the algorithm may automatically plan treatment on the stitched images and recommend where the treatment should start. The physician may also plan treatment from the stitched image data. After the treatment has been planned, the physician may move the transducer to a region that enables the therapy transducer to create the initial elemental treatment volumes within the target. Spatial image correlation techniques may be used to assist the physician in appropriate applicator placement with respect to the target. In this case, current ultrasound images are compared to images already acquired and stored during pre-treatment surveys. Device position sensors (e.g. magnetic sensors) may also be used assist with applicator placement. The device position sensors may also be combined with the image correlation techniques for even better accuracy. After the device has exhausted its ability to create elemental treatment volumes with the current applicator position, the applicator may be manually moved such that image correlation techniques and/or position sensors are used to assist the physician in applicator placement for the next treatment site. By continuing the process, the full extent of the target may be treated. In the second case, manual movement of the applicator to acquire images to visualize the entire target is not necessary. The data set to see the entire target may be acquired in one applicator position; however, the applicator will have to be moved as previously described due to the movement limitations of the therapy device inside the applicator.

Figure 3A:
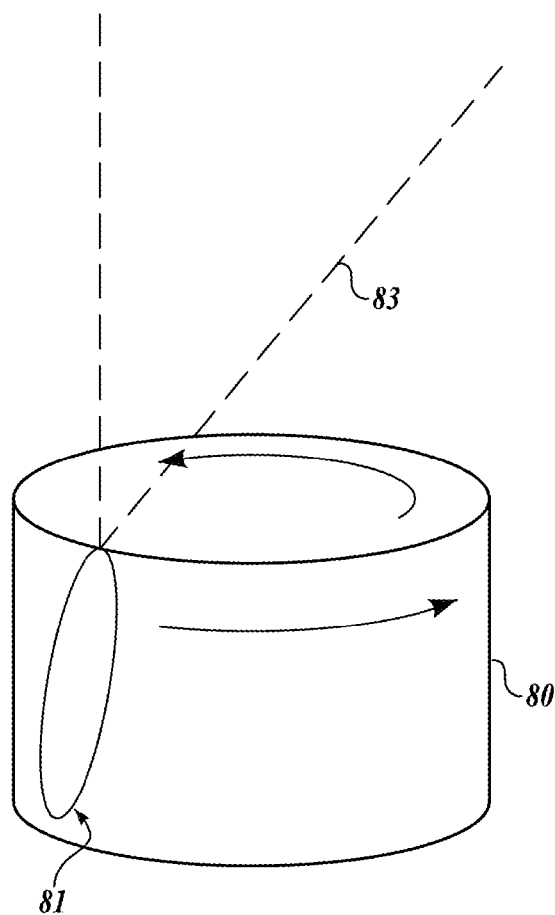
FIGS. 3A and 3B illustrate a cylindrical elemental treatment volume created in accordance with an embodiment of the disclosed technology.
Figure 3B:
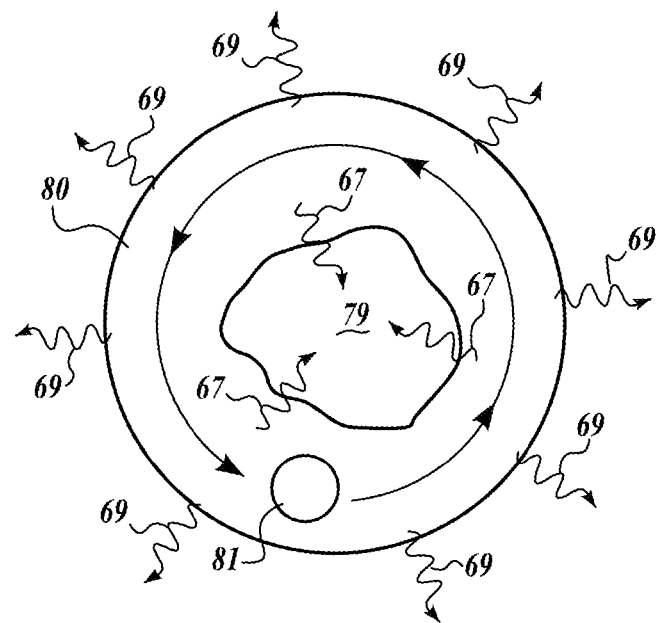

FIGS. 3A and 3B illustrate one exemplary configuration of a cylindrical elemental treatment volume 80 that is used to build up the full desired treatment volume. The elemental treatment volume 80 is created by directing a focal zone 81 of a HIFU beam 83 around the perimeter of the elemental treatment volume. The focal zone 81 can be continuously moved around the perimeter of the elemental treatment volume for one or more times while a HIFU transmitter continually transmits HIFU pulses until the perimeter of the elemental treatment volume 80 is sufficiently ablated. Alternatively, the focal zone 81 can be moved to discrete positions around the perimeter and the HIFU beam 83 pulsed on and off to fully ablate the different positions around the perimeter of the elemental treatment volume.

As shown in FIG. 3B, the elemental treatment volume 80 has a center area 79 that is not directly or is minimally exposed to the focal zone 81 of the HIFU beam 83. This center area 79 is indirectly necrosed by heat conduction created as the perimeter of the elemental treatment volume is ablated. In one particular preferred embodiment, the elemental treatment volume 80 has a diameter of approximately 11 mm. and a height of approximately 10 mm., thereby producing a volume of approximately 1 cc. In this particular preferred embodiment, the volume of the elemental treatment volume is therefore approximately 40 times greater than the volume of the focal zone. Heat from the ablation of the perimeter of the elemental treatment volume is conducted inwards as indicated by the arrows 67 in order to treat the center area 79. At the exterior of the elemental treatment volume, the heat is dissipated outwards as indicated by the arrows 69.

Although the elemental treatment volume 80 shown in FIGS. 3A and 3B is cylindrical in shape, it will be appreciated that other shapes such as spherical or cubic elemental treatment volumes etc. could be created depending on the steering capabilities of the HIFU beam 83.

Figure 3C:
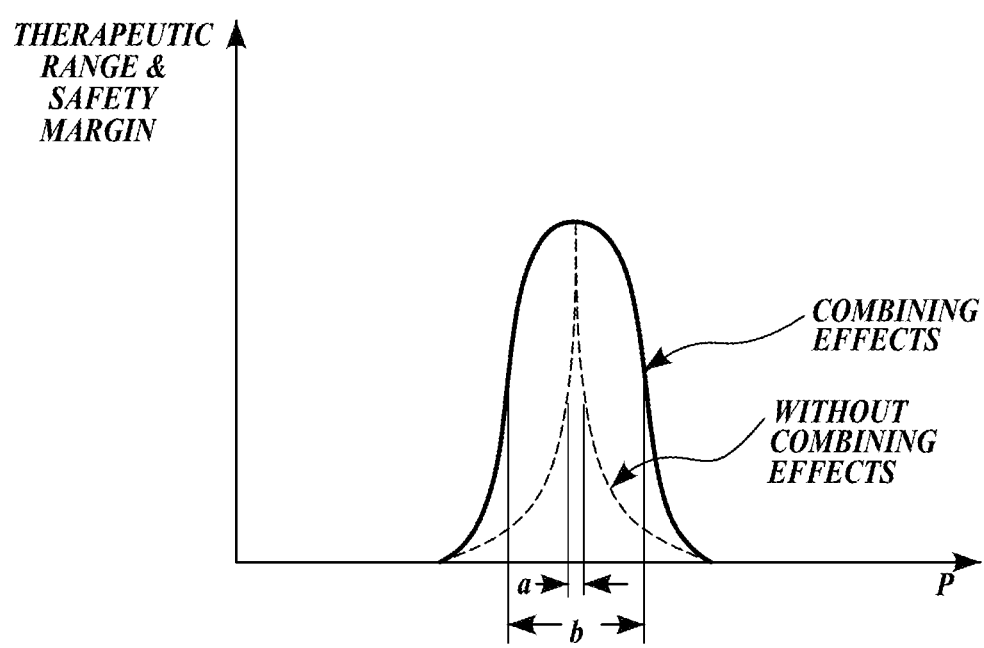
FIG. 3C illustrates a relationship between safety and therapeutic range versus applied power of a HIFU signal.

FIG. 3C conceptualizes the effect of the applied HIFU power level on the resultant therapeutic range and safety margin of a HIFU treatment regimen. With conventional techniques that do not combine the effects of the technology disclosed herein, the range of acoustic power levels where a treatment regimen is both effective and safe can be relatively narrow, as indicated by range "a". That is, small changes to the HIFU power that result in it falling outside the narrow region "a" make the treatment ineffective or possibly unsafe. However, by treating the target tissue using a combined set of effects including one or more of the following (1) focal scanning to produce elemental treatment volumes, (2) inward heat conduction within an elemental volume, and (3) spatial specificity resulting from the application of highly nonlinear acoustic energy with a moderately low fundamental frequency, it is believed that the range of safe and efficacious HIFU power levels can be increased, as indicated by range "b," such that the treatment method is not as sensitive to changes in HIFU power delivered. These various effects acting synergistically to improve HIFU treatment efficiency and collateral tissue safety will be more fully described below.

Figure 3D:
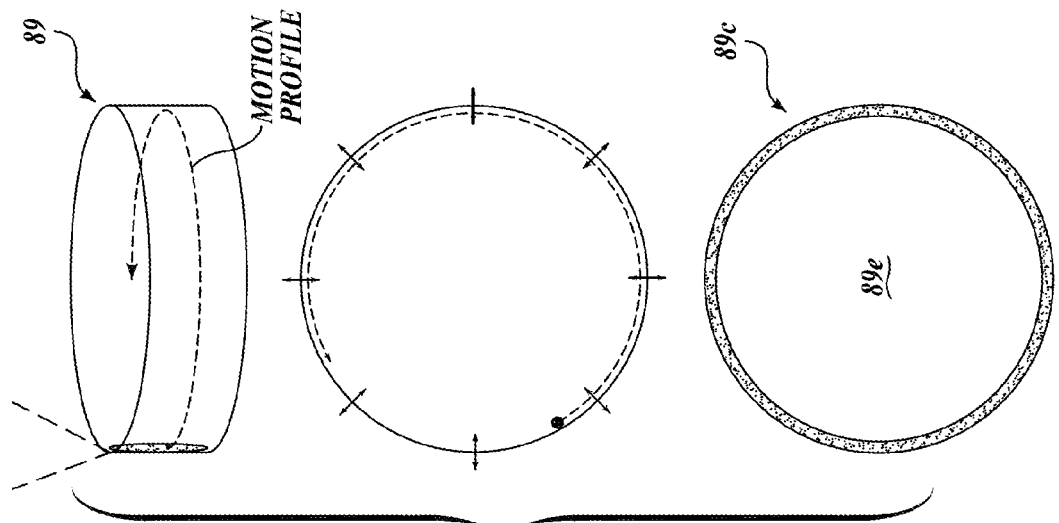
FIG. 3D illustrates the side and top views of an elemental treatment volume that is created in accordance with one embodiment of the disclosed technology, as well as the completely filled-in ablation volume produced by this embodiment.

The size of the elemental treatment volumes can be varied as a function of a variety of factors including the geometry of the devices that will apply the treatment energy. In the embodiment shown in FIG. 3D, an elemental treatment volume 80 is shown in top and side views. This elemental treatment volume is generally cylindrical with a width W and length L that are both approximately equal to the length of the focal zone of the HIFU transducer. As the focal zone is moved around the perimeter of the elemental treatment volume with velocity V, the entire cross-section 80a of the elemental treatment volume is treated due to either direct exposure to the HIFU beam or indirect thermal necrosis caused by inward conduction of heat from the treated perimeter.

Figure 3E:
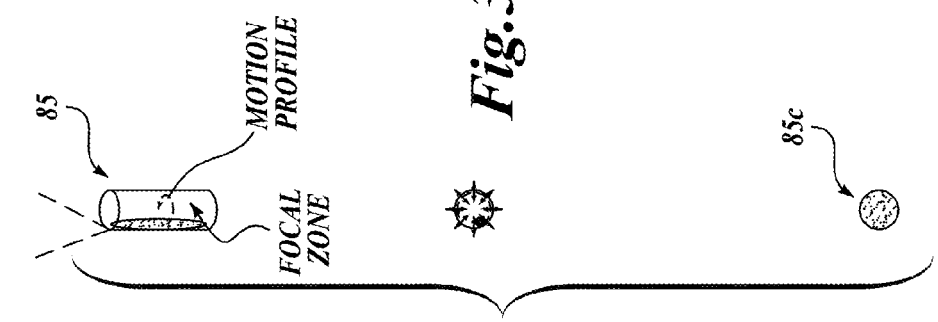
FIG. 3E illustrates the side and top views of a smaller elemental treatment volume that is created in accordance with another embodiment of the disclosed technology, as well as the completely filled-in ablation volume produced by this embodiment.

FIG. 3E shows top and side views of a smaller elemental treatment volume 85 having a diameter that is approximately twice the diameter of the focal zone. With this embodiment, the elemental treatment volume still has well defined boundaries due to the motion of the focal zone around the perimeter of the elemental treatment volume as it is being created. The elemental treatment volume has a cross section 85c that is generally uniformly treated all the way through the interior of the volume. The disadvantage of this elemental treatment volume 85 is that it is small compared with the elemental treatment volume shown in FIG. 3D, and therefore more elemental treatment volumes may be required to treat a desired tissue site.

Figure 3F:
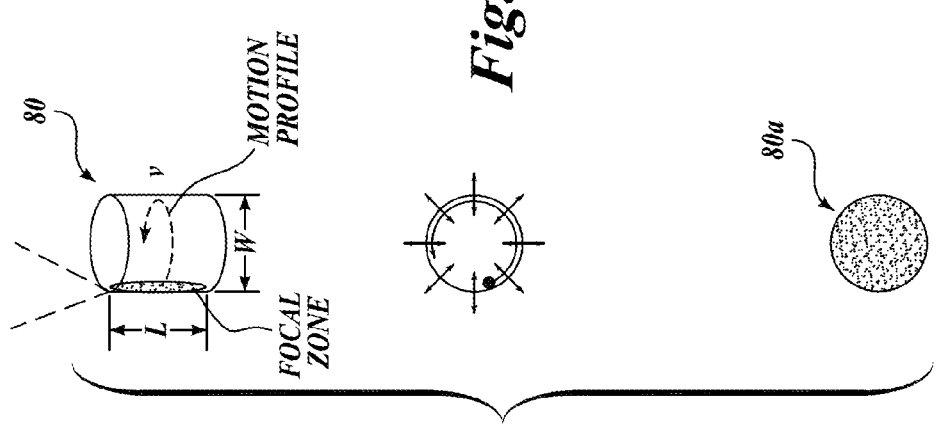
FIG. 3F illustrates the side and top views of a larger elemental treatment volume that is created in accordance with another embodiment of the disclosed technology, as well as the partially filled-in ablation volume produced by this embodiment.

FIG. 3F shows top and side views of yet another elemental treatment volume 89 having a diameter that is significantly larger than the diameter of the focal zone of the HIFU transducer. In this case, cooperative heating of the interior of the elemental treatment volume does not occur and only the perimeter 89c of the elemental treatment volume is ablated. As a result, the interior may not be treated, as depicted by the open center within the ablated ring. While the geometry of the elemental treatment volume 89 is not currently preferred for creating the building blocks used to treat a volume of tissue, the geometry may be useful in creating ablated shells around tissue treatment sites as will be discussed in further detail below. In yet another embodiment, the building blocks (elemental treatment volumes) may be formed of linear segments created by passing the beam for a number of times along their length.

FIG. 3G illustrates a scenario in which the entire dose of treatment energy is applied to the tissue in a single pass of the HIFU focal zone along or around the elemental volume, such that the focal zone passes over each particular point only once and never revisits it. This type of single-pass focal motion can cause rapid deposition of energy and the production of excess heating, which can result in the formation of large focal or pre-focal bubbles in the tissue that reflect the treatment energy and shield distal regions of the treatment volume. The presence of these bubbles can therefore prevent even ablation at all depths along or around the elemental volume. As a result, an uneven or "ragged" treatment pattern 91a is created, having different extents of treated tissue at different points on the distal side of the lesion. In contrast, by distributing the dose of treatment energy over a series of passes along or around the elemental volume using a multiple-pass approach in which the focal zone is directed at each particular point multiple times, spurious formation of large bubbles can be avoided and a more even and uniform treatment pattern 91b is created, such as shown in FIG. 3H. On each pass, a portion of the elemental treatment volume is ablated and the elemental treatment volume begins to "build up" gradually at all points in unison. The multi-pass technique is used in the creation of the elemental treatment volumes, as described below.

FIG. 3I illustrates a technique for creating another embodiment of an elemental treatment volume with an arc or segment-type geometry. This elemental treatment volume can be used to create rings or other shapes with uniform treatment depths and in one method to form a shell around the desired treatment volume. In this embodiment, the focal zone of the HIFU transducer is moved back and forth over a portion (e.g. an arc) of the perimeter. The back-and-forth motion of the HIFU focus results in tissue ablation at uniform depths because it distributes the acoustic energy over a broader region during the treatment, therefore preventing the formation of large focal or pre-focal bubbles that can reflect energy and result in uneven or "ragged" treatment patterns. Multiple treated arcs can therefore be created side by side to complete the treated perimeter of the desired treatment volume.

In each of the examples shown in FIGS. 3A-3B, 3D-3I, the elemental treatment volumes have a height or length that is approximately the same as the length of the focal zone of the HIFU transducer. In some embodiments, the height of an elemental treatment volume may be increased by varying the depth of the focal zone during the application of treatment energy.

In one embodiment described in further detail below, the focal zone 81 of the HIFU beam 83 is steered over the perimeter of the cylindrical elemental treatment volume 80 with a mechanical wobbler at a rate that acts to largely confine the heat within the center 79 of the treatment volume as the elemental treatment volume is being created. The focal zone of the HIFU signal is directed around the perimeter of the elemental treatment volume in such a manner that the interior of the treatment volume is ablated by inward thermal conduction, but the energy deposited beyond its exterior boundary remains below the threshold required for inciting thermal or mechanical damage. Alternatively, the focal zone 81 of the HIFU beam 83 can be steered around the perimeter of the elemental treatment volume with electronic beam steering which, in one embodiment, may be performed by depositing energy at a set of discrete points around the perimeter rather than via continuous sweeping of the focal zone.

To create the elemental treatment volumes described herein, a substantially non-linear pulsed waveform of HIFU energy, such as the waveform 230 shown in FIG. 8B, is applied to the perimeter of the elemental treatment volume. The currently preferred embodiment of this elemental unit volume technique relies on the HIFU treatment waveform being substantially nonlinear in nature, meaning that the originally sinusoidal characteristic of the incident waveform is heavily distorted and no longer sinusoidal in nature by the time it reaches the HIFU focus. The presence of nonlinearity in the focal acoustic waveform is indicative of the conversion of energy from the fundamental acoustic frequency into higher harmonics, which in turn are more readily absorbed by the tissue residing in and immediately adjacent to the focal zone. This effect results in a dramatically increased heating rate that remains tightly localized to the focal region, leading to increased treatment efficacy while maintaining the safety of collateral tissues. The degree of focal waveform nonlinearity favored for this preferred embodiment is that which ensures, at a minimum, the onset of shock in the focal pressure waveform. The onset of shock indicates that at some point along the focal waveform, there is a local pressure discontinuity (i.e., the pressure waveform has an infinitely-valued slope). The degree of focal nonlinearity useful with this preferred embodiment can also be substantially higher as well, extending beyond the point of initial shock onset to include the formation of a fully-developed shock front within the tissue at the HIFU focus, under some conditions within the tissue volume under treatment. In one embodiment, a substantial portion of the energy at the fundamental (e.g. 20% or more) is converted into power at the harmonics of the fundamental frequency of the treatment signals. This level of nonlinearity in the focal HIFU waveform typically occurs in conjunction with pressure amplitudes that may result in the formation of bubbles from either acoustic or thermal origins (e.g., inertial cavitation, stable cavitation, or tissue boiling). The presence of bubbles in the tissue from any of these sources does not adversely affect the efficacy or safety of the elemental treatment volume technique, as long as the multiple-pass focal scanning approach is used to apply the HIFU energy in a distributed fashion across or along all points on the unit volume's periphery during treatment. In fact, the presence of such bubbles can be highly advantageous to enable various feedback techniques if desired, due to the fact that bubble scattering cross-sections can be much larger than their geometric size and therefore allow them to serve as easily-detectable indicators of treatment onset and progression.

Figure 9:
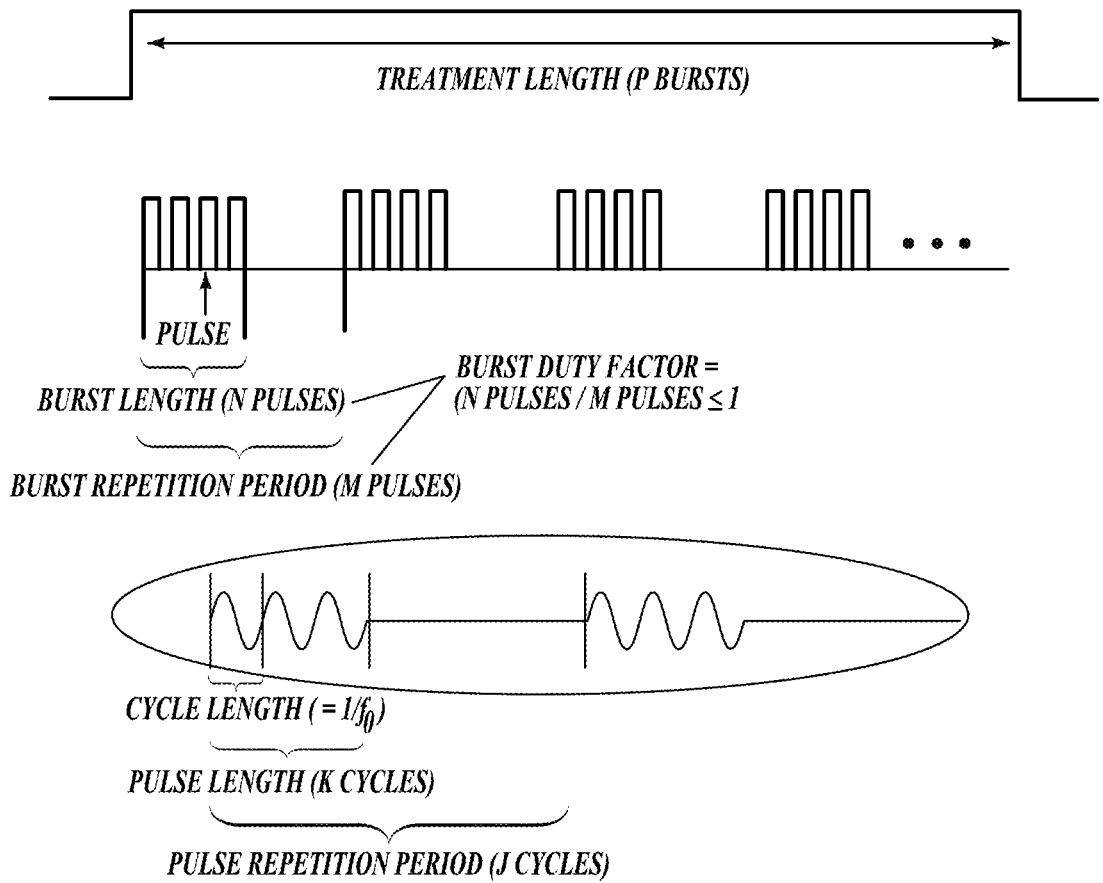
FIG. 9 illustrates a number of adjustable parameters in treatment waveform.

In one particular experimental construct, the most preferred peak acoustic powers used to attain the desired level of nonlinearity in the HIFU focal zone range from 600-3100 watts, depending upon the depth of the particular elemental tissue volume with respect to the body surface, the design of the HIFU transducer, and its power handling capability. These acoustic powers are delivered to the elemental volume in a pulsed fashion, where the most preferred pulses consist of 15-45 cycles at a nominal operating frequency of 1 MHz and are delivered at pulse repetition frequencies (PRFs) of 2-8 kHz. These pulses are then delivered in a series of successive bursts, the total number of which determines the overall treatment time. FIG. 9 illustrates the acoustic timing structure of a HIFU treatment signal. Each treatment signal consists of P bursts of HIFU signals, wherein each burst has N pulses of K cycles at the fundamental frequency ($f_0$) of the HIFU transducer. These bursts of HIFU pulses are then repeated with a burst repetition period of M pulses. The following table illustrates the currently preferred ranges for both the acoustic timing and acoustic power parameters to be used in treating tissue with a HIFU transducer with a 125 mm diameter spherical shell and an F-number of 1. It will be appreciated that the parameters listed may be varied with changes in the depth of tissue to be treated and the specifications of the HIFU transducer to be used.

TABLE 1

Preferred Operating Ranges for Selected Acoustic Timing Parameters

| PARAMETER | Min. | Nominal | Max. | Units |
|---|---|---|---|---|
| Acoustic cycle length (=1/$f_0$) | | | | |
| Most preferred range | 0.8 | 1.0 | 1.2 | µs |
| Less preferred range | 0.65 | 1.0 | 1.35 | µs |
| Least preferred range | 0.5 | 1.0 | 1.5 | µs |
| Pulse length (number of cycles) | | | | |
| Most preferred range | 15 | 30 | 45 | cycles |
| Less preferred range | 10 | 30 | 50 | cycles |
| Least preferred range | 5 | 30 | 55 | cycles |
| Pulse repetition frequency (PRF) | | | | |
| Most preferred range | 2.0 | 4.0 | 8.0 | kHz |
| Less preferred range | 1.0 | 4.0 | 12.0 | kHz |
| Least preferred range | 0.5 | 4.0 | 18.0 | kHz |
| Burst length (number of pulses) | | | | |
| Most preferred range | 400 | 500 | 600 | pulses |
| Less preferred range | 250 | 500 | 750 | pulses |
| Least preferred range | 100 | 500 | 900 | pulses |
| Burst duty factor | | | | |
| Most preferred range | 40 | 50 | 60 | % |
| Less preferred range | 25 | 50 | 75 | % |
| Least preferred range | 10 | 50 | 90 | % |
| Treatment duration per unit volume | | | | |
| Most preferred range | 10 | 25 | 50 | s |
| Less preferred range | 8 | 25 | 75 | s |
| Least preferred range | 5 | 25 | 100 | s |

TABLE 2

Preferred Operating Ranges for Acoustic Power as a Function of Tissue Depth
(TRANSDUCER: 125 MM SPHERICAL SHELL, F-NUMBER = 1.0)

| PARAMETER | Min. | Nominal | Max. | Units |
|---|---|---|---|---|
| Pulse-Average Acoustic Power, Treatment Depth of 20-30 mm | | | | |
| Most preferred range | 600 | 750 | 900 | W |
| Less preferred range | 475 | 750 | 1025 | W |
| Least preferred range | 375 | 750 | 1125 | W |
| Pulse-Average Acoustic Power, Treatment Depth of 30-40 mm | | | | |
| Most preferred range | 725 | 900 | 1075 | W |
| Less preferred range | 575 | 900 | 1225 | W |
| Least preferred range | 450 | 900 | 1350 | W |
| Pulse-Average Acoustic Power, Treatment Depth of 40-50 mm | | | | |
| Most preferred range | 850 | 1050 | 1250 | W |
| Less preferred range | 675 | 1050 | 1425 | W |
| Least preferred range | 525 | 1050 | 1575 | W |
| Pulse-Average Acoustic Power, Treatment Depth of 50-60 mm | | | | |
| Most preferred range | 1025 | 1275 | 1525 | W |
| Less preferred range | 825 | 1275 | 1725 | W |
| Least preferred range | 650 | 1275 | 1925 | W |
| Pulse-Average Acoustic Power, Treatment Depth of 60-70 mm | | | | |
| Most preferred range | 1370 | 1525 | 1670 | W |
| Less preferred range | 1220 | 1525 | 1820 | W |
| Least preferred range | 1060 | 1525 | 1980 | W |
| Pulse-Average Acoustic Power, Treatment Depth of 70-80 mm | | | | |
| Most preferred range | 1450 | 1800 | 2150 | W |
| Less preferred range | 1175 | 1800 | 2425 | W |
| Least preferred range | 900 | 1800 | 2700 | W |
| Pulse-Average Acoustic Power, Treatment Depth of 80-90 mm | | | | |
| Most preferred range | 1725 | 2150 | 2575 | W |
| Less preferred range | 1400 | 2150 | 2900 | W |
| Least preferred range | 1075 | 2150 | 3225 | W |
| Pulse-Average Acoustic Power, Treatment Depth of 90-100 mm | | | | |
| Most preferred range | 2050 | 2575 | 3100 | W |
| Less preferred range | 1675 | 2575 | 3475 | W |
| Least preferred range | 1300 | 2575 | 3875 | W |

While the HIFU transmitter is applying energy of these specifications, a cylindrical elemental treatment volume is created by mechanically wobbling the HIFU focus, which is approximately 10 mm. in length and 2 mm. in width in FWHM dimensions in one embodiment, around a trajectory with a most-preferred diameter of 8-12 mm at a rate of nominally 2 Hz. In this case, the diameter around which the HIFU focus rotates is approximately equal to the HIFU focal zone length and five-fold greater than the HIFU focal zone width. The mechanical wobbling and HIFU treatment continue in this fashion for a total treatment duration of 10-50 seconds per elemental volume, in the most-preferred embodiment. The treatment duration per unit volume depends on the tissue depth at which the particular elementary volume is created, as well as the overall treatment volume desired. For example, larger overall treatment volumes typically require less treatment time per unit volume, due to the advantages of cooperative heating among many neighboring unit volumes. Similarly, unit volumes created in shallow layers that abut previously-treated deeper layers typically require less time to ablate, owing to modest "preheating" of the shallow layers that occurs while the deeper layers are being treated. Arbitrarily large treatment volumes can then be achieved by successive "stacking" of layers composed of some number of these elemental treatment volumes, with a most-preferred axial separation between adjacent layers of 8-12 mm. The following table summarizes the preferred ranges of focal motion parameters for use in conjunction with the acoustic waveforms and powers described above.

TABLE 3

Preferred Operating Ranges

| for Selected Focal Motion Parameters | Min. | Nominal | Max. | Units |
|---|---|---|---|---|
| Focal wobble diameter | | | | |
| Most preferred range | 8 | 10 | 12 | mm |
| Less preferred range | 6 | 10 | 15 | mm |
| Least preferred range | 4 | 10 | 20 | mm |
| Focal wobble revolution rate | | | | |

TABLE 3-continued

Preferred Operating Ranges

| for Selected Focal Motion Parameters | Min. | Nominal | Max. | Units |
|---|---|---|---|---|
| Most preferred range | 1.8 | 2 | 2.2 | Hz |
| Less preferred range | 1 | 2 | 4 | Hz |
| Least preferred range | 0.25 | 2 | 8 | Hz |
| Axial separation between adjacent layers | | | | |
| Most preferred range | 8 | 10 | 12 | mm |
| Less preferred range | 6 | 10 | 15 | mm |
| Least preferred range | 4 | 10 | 20 | mm |

Although the currently preferred embodiment uses a pulsed waveform which is non-linear at the focal zone, it will be appreciated that a continuous-wave (CW) or linear HIFU signal such as the waveform 232 shown in FIG. 8A may also be used, depending on the power level used and the rate at which the focal zone is moved.

Though this previous example specifies the use of a 2 Hz mechanical rotation rate around the perimeter of the elemental volume, both lower and higher rates could be used to ablate these types of elemental volumes. However, if too low a rate is used, the heat developed to ablate the perimeter of the elemental treatment volume may not be sufficiently contained within the interior of the elemental volume and may result in adverse effects in collateral tissues. Higher rotation rates may require the use of an electronic beam former instead of mechanical rotation and may also affect the HIFU treatment power necessary. If electronically steered, the beam may, in one embodiment, be focused at a set of discrete points around the perimeter, rather than continuously swept. As indicated in the above table, in one embodiment, the mechanical rotation rate of the HIFU focus about the unit volume diameter is at least 0.25 Hz. In another more preferred embodiment, this rotation rate is at least 1 Hz, while in the most preferred embodiment this rate is nominally 2 Hz. Regardless of the rotation rate used, it is preferable to apply energy over a number of passes (e.g. two or more) around the perimeter using a multiple-pass approach at a rate and power level that allows the entire elemental treatment volume to be ablated in unison, in order to achieve symmetric geometry in the shape of the ablated elemental volume. Otherwise, with a single-pass approach in which the focal zone is scanned relatively slowly to achieve ablation without having to revisit a particular point, the excess heating produced may cause large focal or pre-focal bubbles to form that can cause shielding and distortion, preventing the production of an evenly ablated tissue site, as illustrated in FIG. 3G-3H and described previously. Again, it should be noted that even though large focal or pre-focal bubbles can detract from the uniformity of treatment when a single-pass approach is used, the presence of bubbles in the tissue from either acoustic or thermal origins does not adversely affect treatment efficacy as long as the HIFU focus is scanned along or around the unit volume using multiple passes to temporally distribute the treatment energy directed at any one point in the volume.

As will be appreciated, the size of the elemental treatment volume is preferably selected so that a center region 79 can be indirectly treated while not unduly increasing the treatment time required to treat a desired volume of tissue. If the size of the elemental treatment volume is too large, the center region 79 will not be ablated by effective conduction of heat into the interior of the volume. Conversely, if the size of the elemental treatment volume is too small, then the time required to treat the desired treatment volume must be adjusted to avoid over-dosing the elemental volume and potentially causing damage to collateral tissues. In addition, the time to create each elemental treatment volume may decrease as the focal zone is moved proximally toward the surface of the body, due to the residual heat persisting in the treatment volume from ablation of the more distal elemental volumes.

In a currently preferred embodiment, the method of creating the elemental treatment volumes takes advantage of several features of HIFU therapy resulting from the synergistic effects of highly-nonlinear acoustic waveforms and the mechanical or electronic motion of the HIFU focus about the perimeter of the unit volume. These combined effects comprise a set of operating points that result in the enhanced safety and efficacy observed when using this treatment method. This set of operating points includes a combination of the following: (1) The elemental treatment volume is ablated in such a way that the interior region is primarily destroyed through inward conduction of heat, not direct ablation by HIFU. This feature enlarges the size of the elemental volume without increasing the HIFU dose that has to be delivered to the tissue to do so. (2) The motion of the HIFU focal zone about the elemental treatment volume perimeter is accomplished by making multiple passes around the perimeter using a specified rotation rate, as opposed to making one a single pass around the circumference of the unit volume to achieve ablation. This feature allows the tissue within the elemental treatment volume to be ablated with uniform, smooth boundaries and equal length at substantially all points around the perimeter. (3) The elemental treatment volume is subjected to highly concentrated acoustic energy only in the focal region of the HIFU beam by virtue of the use of a highly nonlinear acoustic waveform that dramatically enhances the heating rate in the focal zone. (4) The fundamental acoustic frequency of the HIFU applicator is kept low enough to ensure safe propagation through untargeted collateral tissues. As a result of the system's ability to create substantially uniform elemental treatment volumes despite changes in tissue characteristics or the presence of bubbles in the focal zone, the treatment system can operate without reliance on temperature feedback monitoring, thereby resulting in faster treatment and reduced system complexity and cost. The combination of all these attendant benefits ensures adequate efficacy of the treatment, obviating the need for thermometric techniques to determine the temperature within the treatment volume to verify that temperature levels required for thermal necrosis are being achieved. Additionally, the combination of the feature set described above takes advantage of synergistic effects that allow each unit volume to be ablated with precise boundaries and minimal thermal invasiveness to collateral tissues outside the treatment volume.

Figure 3J:
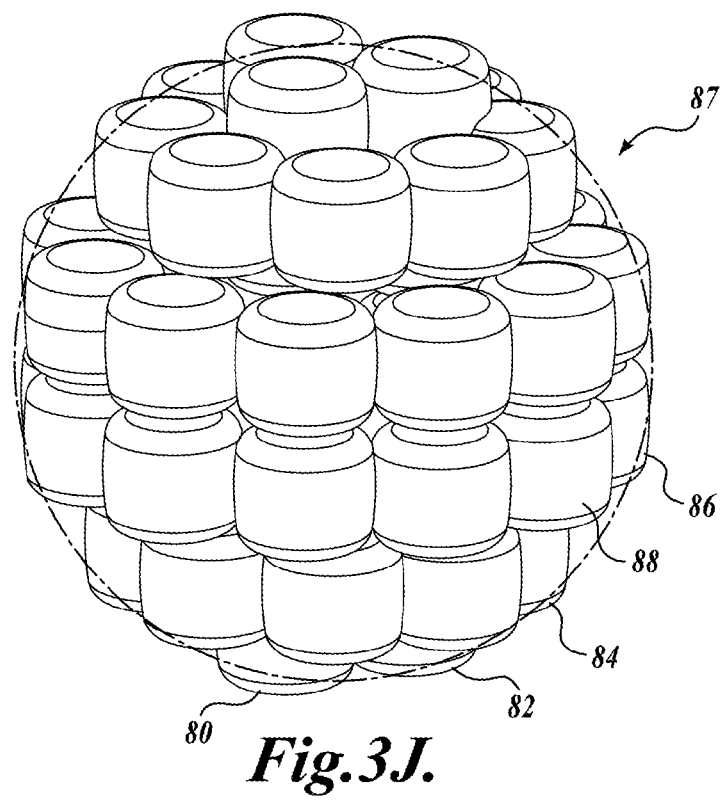
FIGS. 3J and 3K illustrate a technique for creating an ablated shell around a tissue volume from a number of elemental treatment volumes in accordance with an embodiment of the disclosed technology.
Figure 3K:
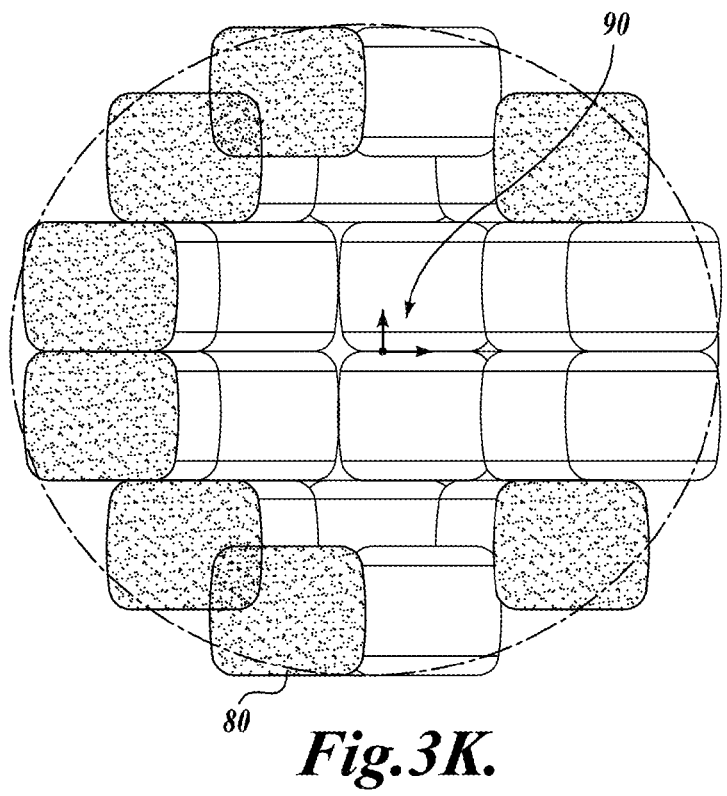

By amassing the full treatment volume from "building blocks" of elemental treatment volumes, arbitrarily-sized volumes can be ablated with the same inherent spatial precision and heat confinement afforded to each constituent unit volume. FIGS. 3J and 3K illustrate one technique for using the elemental treatment volumes 80 to treat a desired volume of tissue. In this embodiment a three dimensional pattern of adjacent elemental treatment volumes are created such that together they form an ablated shell that surrounds all or a portion of a desired tissue treatment volume. In the embodiment shown in FIGS. 3J and 3K, an ablated shell 87 is formed from a number of smaller ablated elemental treatment volumes 80, 82, 84, 86, 88 etc. Each of the elemental treatment volumes is created sufficiently close together to form a necrosed shell or barrier of ablated tissue between the encapsulated tissue and its blood supply. As shown, the elemental treatment volumes 80, 82, 84, 86, 88 etc. are created adjacent to each other in annular patterns of increasing internal diameter that extend from the distal end of the desired tissue treatment volume to approximately midway in the tissue volume, where the diameter of the treatment volume is the largest. The diameter of the annular patterns then progressively decreases towards the proximal end of the tissue volume to be treated. Together the annular patterns create a shell with a "hollow" interior space 90 that encapsulates a portion of the desired tissue volume to be treated. With the elemental treatment volumes placed sufficiently close to each other, blood supplied to the fibroid or other tissue to be treated is cut off, or is substantially reduced so that the tissue will ischemically necrose when left in the body. In addition, some or all of the tissue within the center of the shell may necrose due to heat conduction when the shell is being created. Because the entire treatment volume is not ablated, there is less possibility that excess heat will be created in the body which may damage untargeted tissue and the treatment time is significantly reduced from that required if the entire volume were to be directly ablated. In one experiment using the technology described herein, a 5 cm. diameter treatment volume in an in-vivo porcine thigh was treated by forming a shell of 20 elemental treatment volumes around the surface of the ball in approximately 320 seconds, where each elemental treatment volume has a volume of approximately 1 cubic cm. In one embodiment the individual elemental treatment volumes in each layer of the shell are created in a pattern such that adjacent elemental treatment volumes are not created sequentially. In other words, the pattern of elemental treatment volumes in each layer of the shell is created in a manner that maximizes the distance between two sequentially created elemental treatment volumes.

Although the shell 87 illustrated in FIGS. 3J and 3K is shown as being hollow, it will be appreciated that it in some circumstances it may be desirable to create one or more elemental treatment volumes within the interior of the shell to actively necrose some or all of the tissue inside the shell 87. The number and spacing of the elemental treatment volumes can be decided by the physician based on experience, the time available for treatment, the type of tissue being treated or other factors. Alternatively, a processor can be programmed to determine if the interior of the shell should be empty or filled with one or more elemental treatment volumes.

The shell 87 is shown in FIG. 3J as being substantially sealed about its outer surface. However, it will be appreciated that a shell 87 can still be created even if there are gaps between the individual elemental treatment volumes. How close the elemental treatment volumes are placed in order to create the shell may be based on the type of tissue being treated, the thermal conductivity of the tissue, its absorption characteristics, or other factors.

As will be appreciated, other patterns besides shells of elemental treatment volumes can be used to treat the desired tissue volume. For example, layers of horizontally spaced adjacent elemental treatment volumes can be created in the desired tissue volume. The distance between elemental treatment volumes in a layer can be closely spaced or more spread apart.

Figure 4A:
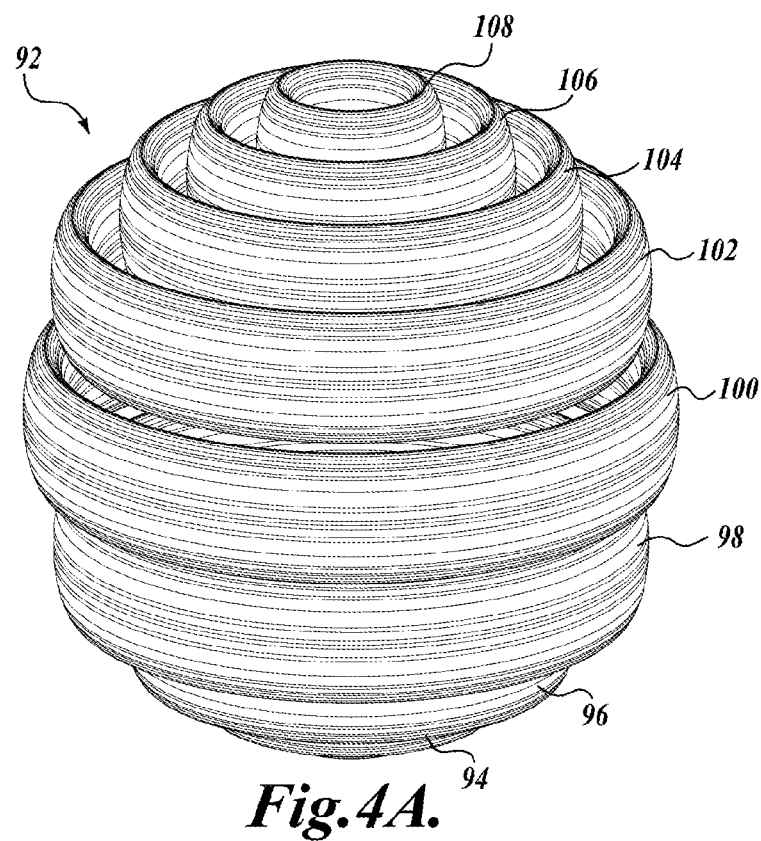
FIGS. 4A and 4B illustrate a second technique for creating an ablated shell around a tissue volume in accordance with another embodiment of the disclosed technology.
Figure 4B:
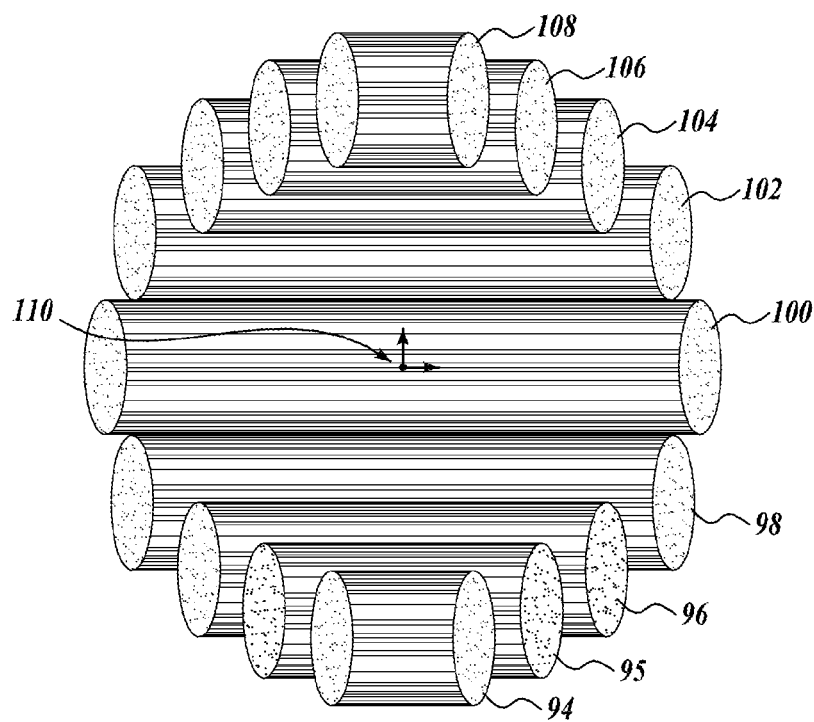

FIGS. 4A-4B show an alternative technique for creating an ablated shell 92 around a tissue volume in accordance with the disclosed technology. In this embodiment, an ablated shell comprises a stacked series of toroids, each having a varying internal diameter. A toroid 94 of minimum internal diameter (or a solid disk) is placed at the distal end of the tissue to be treated with respect to the HIFU transducer. Additional toroids are created proximally to the distal toroid 94, including toroids 95, 96, 98 of increasing diameter up to a toroid 100 where the toroid has a maximum internal diameter. The internal diameters of the toroids then get progressively smaller with toroids 102, 104, 106 as the HIFU focal zone is moved more proximally before closing the shell 92 with a toroid 108 of minimum internal diameter (or a solid disk) at the most proximal location in the treatment volume. As can be seen in FIG. 4B, the interior of each of the toroids 94-108, when stacked, define a shell with a "hollow" (i.e. un-ablated) region 110 that encapsulates a volume of the tissue to be treated and isolates it from its blood supply. In one embodiment, the outer diameter of the toroids 94-108 is selected to correspond to the outer dimension of the fibroid in order to minimize the volume of tissue that is directly ablated with HIFU. In another embodiment, the outer diameters of the toroids 92-106 are selected to be within a set distance internal to the fibroid's outer boundary in order to allow the fibroid tissue external to the ablated shell 92 to be partially or completely destroyed via thermal necrosis (due to heat conducted from the ablated shell 92) and/or secondary injury pathway mechanisms (ischemia, inflammation, apoptosis, et. al.). In yet another embodiment, the inner diameters of the toroids 94-108 correspond to the outer diameter of the tissue volume such that the interior 110 of the ablated shell 92 created is slightly larger than the tissue volume, perhaps allowing a more complete kill of tumor tissue at the expense of killing a small amount of surrounding healthy myometrium. Another advantage of such an embodiment is the ability to create the ablated shell 92 such that it overlaps the endometrial lining, thus necrosing at least some of the nearby endometrium which may reduce menorrhagia symptoms.

Figure 4C:
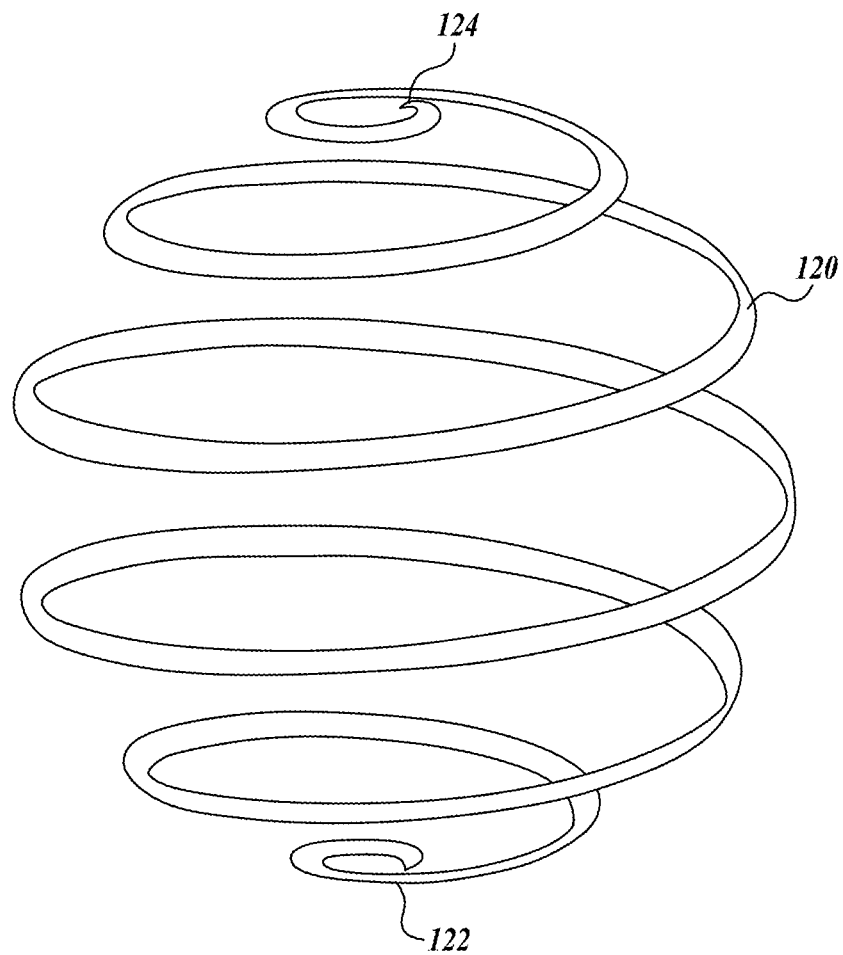
FIG. 4C illustrates a third technique for creating an ablated shell around a tissue volume in accordance with another embodiment of the disclosed technology.

FIG. 4C shows yet another embodiment of an ablation pattern that creates an ablated shell to encapsulate a tissue volume and isolate it from an external blood supply. In the embodiment shown, an ablated shell is created from a spiral pattern 120. The spiral has a minimum diameter at a distal end 122 of the tissue volume to be treated, expands to a maximum diameter at approximately the midpoint of the tissue volume, and then progressively decreases in diameter towards the proximal end 124 of the tissue volume. Each loop of the spiral pattern 120 is sufficiently close to an adjacent loop that the tissue is actively necrosed in order to create an ablated shell around a tissue volume that cuts off the tissue in the shell from its blood supply. As will be appreciated, the spiral pattern 120 could also be used to create the smaller elemental treatment volumes described above and shown in FIGS. 3A and 3B depending on the size of the focal zone of the HIFU transducer and the desired size of the elemental treatment volumes.

Figure 4D:
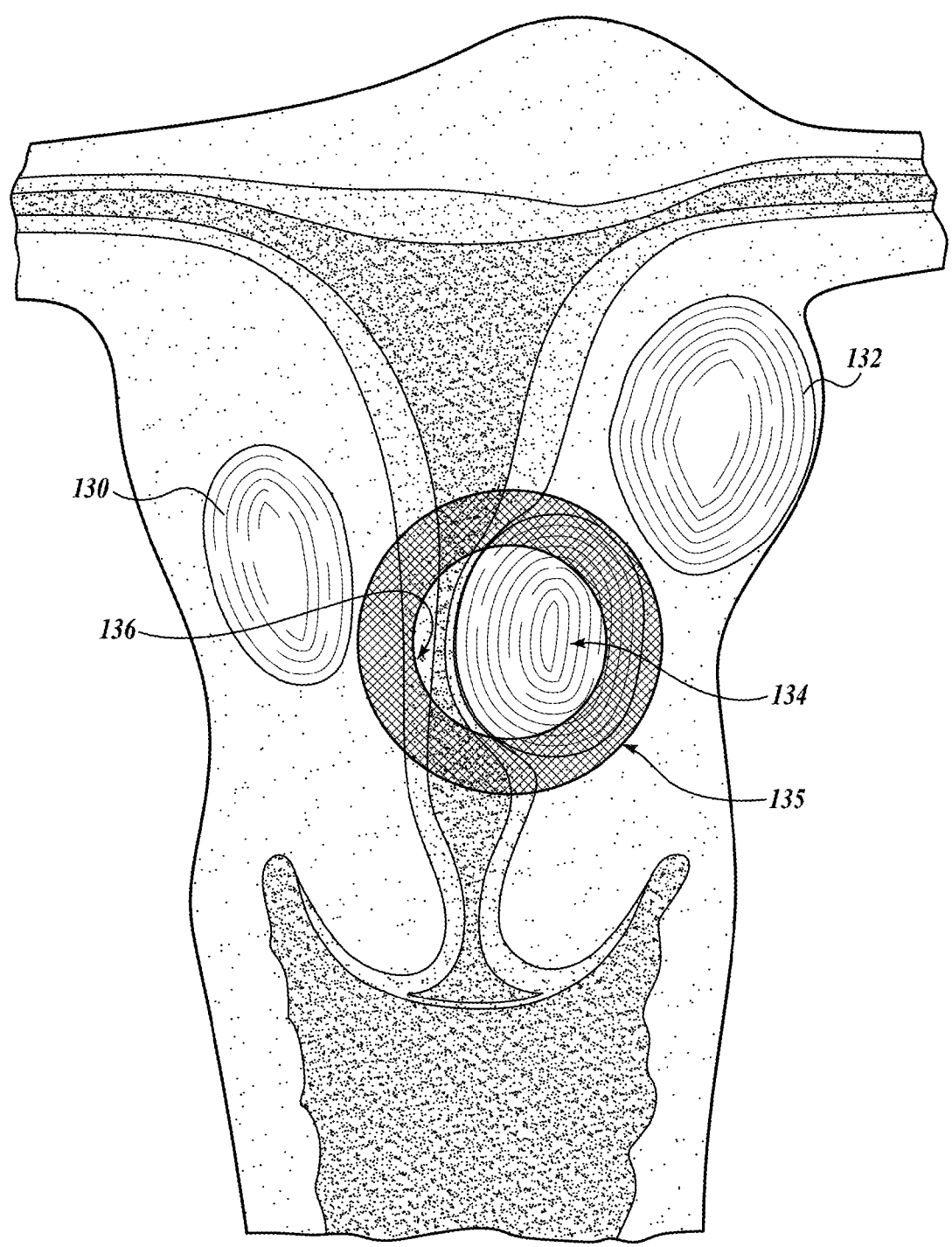
FIG. 4D illustrates a technique for creating an ablated shell around a uterine fibroid, which overlaps at least a portion of the adjacent endometrium, so as to further reduce menorrhagia symptoms.

FIG. 4D illustrates a uterus having three different types of fibroids including an intramural fibroid 130, a subserosal fibroid 132, and a submucosal fibroid 134. In the example shown, an ablated shell 135 is created to encapsulate the entire submucosal fibroid 134 on one side of the uterine wall as well as a portion of the nearby endometrium tissue 136 on the opposite uterine wall. By creating the ablated shell 135 to encapsulate not only the fibroid 134 but also a portion of the adjacent endometrium 136, menorrhagia symptoms may be reduced.

Although the shape of the ablated shells is shown as being generally spherical in FIGS. 3J-3K, 4A-4B and 4C, it will be appreciated that other shapes, such as conical or double conical, ovoid (e.g., egg shaped), or rectangular could be used. The particular shape of the shell created may depend on the shape of the tissue volume to be treated and the ability of the equipment used to steer the focal zone of the HIFU transducer in a desired pattern. Any shell shape of ablated tissue that forms a barrier between tissue internal to the shell and its external blood supply will function to allow the encapsulated tissue to ischemically necrose when left in the body. It will also be appreciated that, as an alternative to ablating an excessively large or irregularly shaped shell, one could ablate two or more regularly-shaped shells adjacent to each other to treat most or all of the desired volume (e.g., 2 spherical shells could be ablated side-by-side inside an oblong tumor, rather than ablating one oblong shell). If numerous shells are created within the tissue volume, one can also form a matrix (or "honeycomb") of ablated elemental tissue volumes with interspersed regions of non-ablated tissue which subsequently ischemically necrose in situ. Such a matrix could involve regular or random spacing of ablated elemental treatment volumes to accomplish the same effect, and the matrix could consist of numerous closed shells (e.g., spherical shells) or layers of stacked/overlapping elemental treatment volumes.

Those skilled in the art will readily appreciate that other advantages of the shell ablation approach are (1) increased treatment rate, since energy is applied to only a sub-volume of the tissue ultimately treated, (2) a larger treatment size for a given allotment of treatment time, (3) and less energy required, compared to that which would be used if the entire volume including its interior were directly ablated. Automating a HIFU system to ablate a symmetrical (e.g., spherical) shell will reduce demands on a user with regard to imaging, targeting and probe manipulation. If shell is symmetrical, the user can easily visualize its projected relationship to tumor boundaries as visualized with an imaging mechanism such as an ultrasound imager, MRI, x-ray, etc. The user need only manipulate the HIFU system so as to center an overlay of the projected shell within the image of the target tissue, expand the diameter of the shell to desired dimensions (e.g., just inside periphery of the tumor), and then hold the system stationary relative to the target tissue while the system automatically ablates the specified shell pattern.

Figure 5:
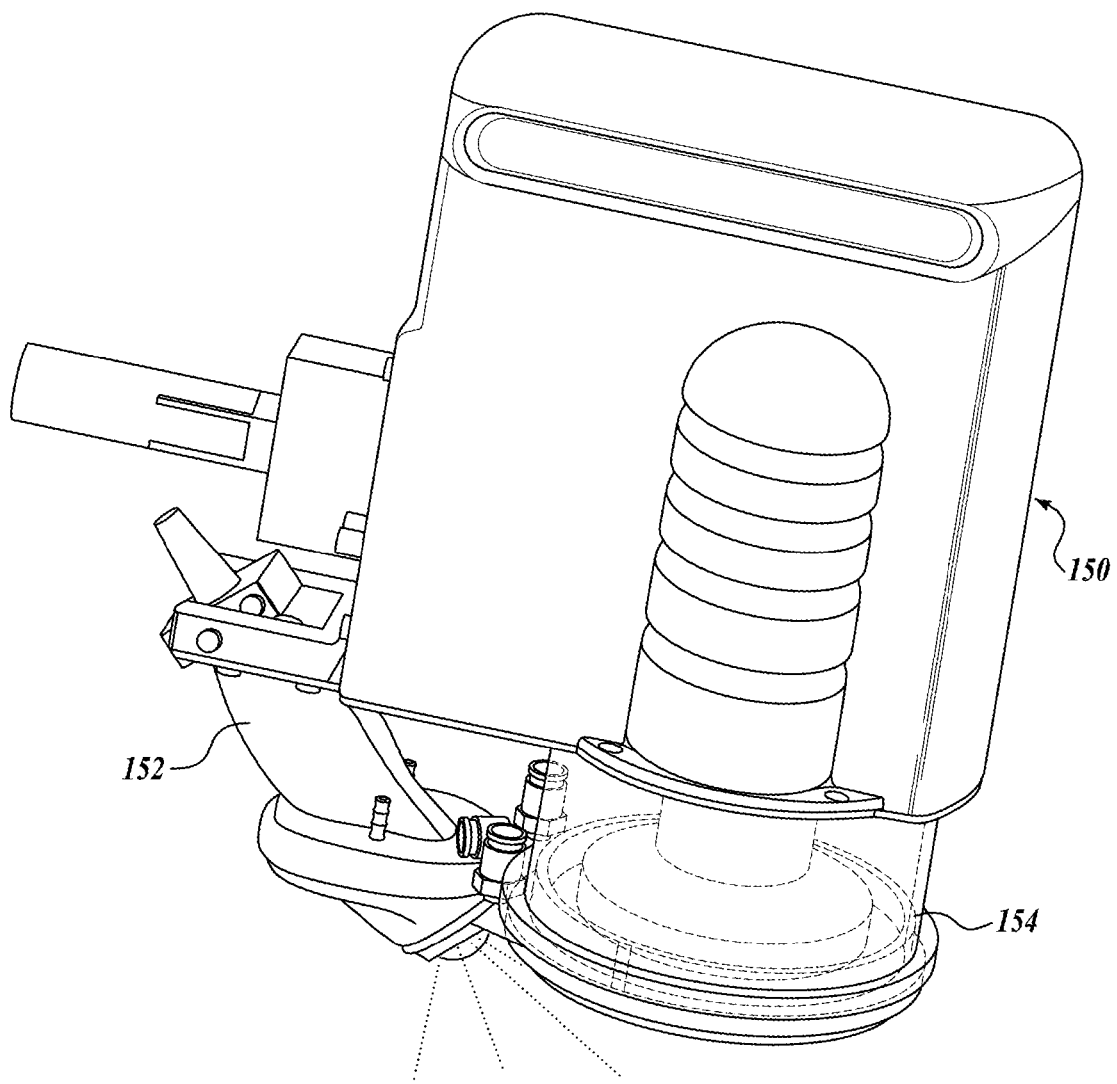
FIG. 5 illustrates a HIFU treatment device in accordance with one embodiment of the disclosed technology.

FIG. 5 shows one embodiment of a HIFU treatment device that can be used to treat tissue in the manner described above. The HIFU treatment device 150 is a hand held or hand guided applicator device that includes an imaging transducer 152 and a HIFU transducer 154. The imaging transducer 152 is fixed in position to capture images of tissue within a body that includes the focal zone of the HIFU transducer 154. As will be explained in further detail below, the focal zone of the HIFU transducer 154 can be mechanically and/or electrically steered to ablate a number of elemental treatment volumes that are adjacently positioned to create a shell that surrounds or encapsulates a desired tissue volume or to create another pattern. While holding the treatment device 150 steady at the desired location, as determined from an image produced from signals obtained from the imaging transducer 152, the focal zone of the HIFU transducer 154 is moved in such a way as to ablate a pattern of elemental treatment volumes in order to create a shell around the treatment volume or to create another pattern of elemental treatment volumes.

The treatment device 150 is coupleable to other components of the treatment system including an image processor and display required to operate the imaging transducer 152 and produce images of the tissue volume. A signal source required to drive the HIFU transducer and a computer to orient the focal zone of the HIFU transducer in a pattern to create the elemental treatment volumes in a desired pattern such as a shell around the tissue volume are also included.

Figure 6:
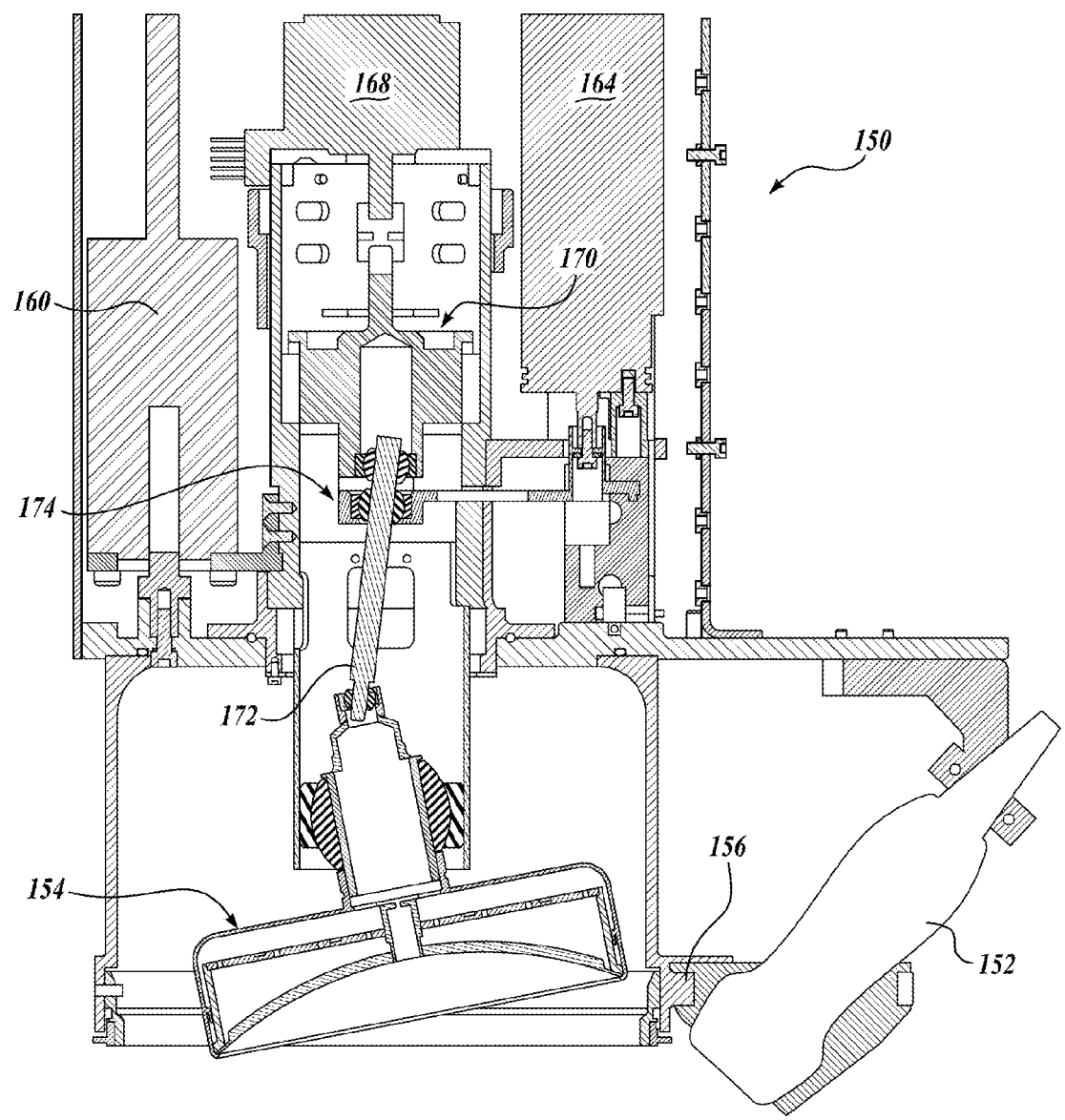
FIG. 6 illustrates one mechanism for varying a position and orientation of a focal zone of a HIFU transducer in accordance with one embodiment of the disclosed technology.

FIG. 6 illustrates one embodiment of a more detailed mechanism for treating the internal body tissues with HIFU signals to create a series of elemental treatment volumes in a shell or other pattern. The treatment device 150 includes a HIFU transducer 154. In the embodiment shown, the HIFU transducer 154 has a fixed focal zone, as defined by the curvature of the piezoelectric elements that comprise the transducer head. A flexible membrane that does not significantly reflect HIFU signals is positioned in front of the HIFU transducer to form a chamber in which liquid can be introduced, stored, and/or circulated. A liquid such as water or de-gassed water then fills the liquid chamber and surrounds the transducer 154 to serve as an acoustic couplant to the tissue. A port 156 connects the treatment device to a pump to allow the liquid of a constant volume to flow around the HIFU transducer.

To adjust the depth of the focal zone where the HIFU signals are delivered to the patient, a linear actuator 160 or motor raises or lowers the HIFU transducer 154 within a housing of the treatment device 150 via a threaded rod or other mechanism. By adjusting the height of the transducer 154 within the housing, the depth where the HIFU signals are delivered within the body can be controlled.

In addition, the treatment device 150 includes an offset bearing 170 that, when rotated by a motor 168, wobbles an end of a shaft 172 around the center of the offset bearing 170. The HIFU transducer 154 is coupled to the other end of the shaft 172 through a slidable bearing. A linear actuator 164 or motor positions a spherical bearing 174 that surrounds the shaft 172 towards or away from the offset bearing 170. The position of the spherical bearing 174 on the shaft 172 controls the angular orientation of the focal zone of the HIFU transducer 154.

Figures 6A, 6B:
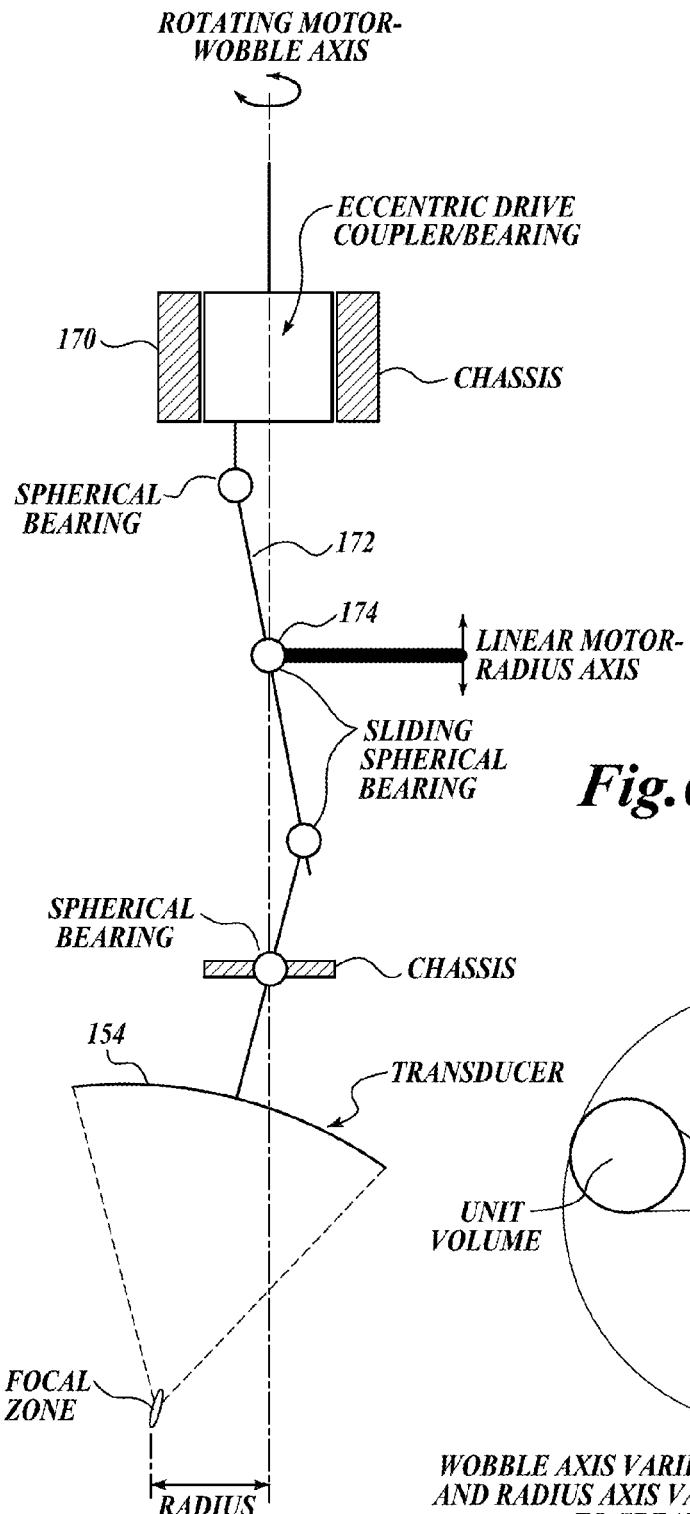
FIGS. 6A and 6B illustrate how the angular orientation of the focal zone is changed with the mechanism shown in FIG. 6.

As shown in FIGS. 6A and 6B, by turning the shaft of the motor 168 and by changing the angular orientation of the focal zone of the HIFU transducer by adjusting the position of the spherical bearing 174 along the length of the shaft 172, toroidal rings of ablated tissue or annular patterns composed of ablated cylinders/spheres can be created in the body at various depths.

If the motors 164 and 168 are simultaneous rotated back and forth through a desired angle with signals that are approximately 90 degrees out of phase, the focal zone of the HIFU transducer will trace out a substantially circular pattern off a central axis of the treatment device 150, thereby allowing the creation of an elemental treatment volume at a desired location in the body as shown in FIG. 6B. By continuously rotating the motor 168 while the spherical bearing 174 is at the farthest point from the motor 168, the elemental treatment volume can be created at the top and bottom of the shell depending on the depth of the focal zone.

In one embodiment, to treat a desired tissue volume, a physician obtains an image of the tissue volume with the imaging transducer 152 and adjusts the radius of a marker ring on the image or interacts with some other graphical user interface or keyboard to define the boundaries of the desired shell. Based on the radius of the marker ring, a computer calculates the volume or shape of the ablated shell to be created in the body. The HIFU transducer and motors within the treatment device 150 are then activated such that a pattern of elemental treatment volumes is ablated to form the shell that surrounds or encapsulates the tissue volume or some other desired pattern of elemental treatment volumes.

When creating elemental treatment volumes, the focal zone of the HIFU transducer may be continually moved until a treatment volume is ablated or the focal zone may be moved to discrete positions around the perimeter of the elemental treatment volumes and a HIFU signal applied to create the elemental treatment volumes.

In another embodiment, the linear actuator 160 that adjusts the focal zone depth, the linear actuator 164 that adjusts the angle of the HIFU transducer, and the motor 168 that rotates the shaft 172 are simultaneously operated to create a spiral shell ablation pattern of the type shown in FIG. 4C.

Following treatment, the patient may be injected with a contrast agent to allow the physician to confirm that blood perfusion has been appropriately reduced or eliminated within the targeted tissue volume. Non-perfusion would provide a strong indication that the treated tissue volume will undergo (or has undergone) ischemic necrosis. Such contrast agents are well known in the art for use with various different imaging modalities including ultrasound, MRI, x-ray, CT, etc.

Figure 6C:
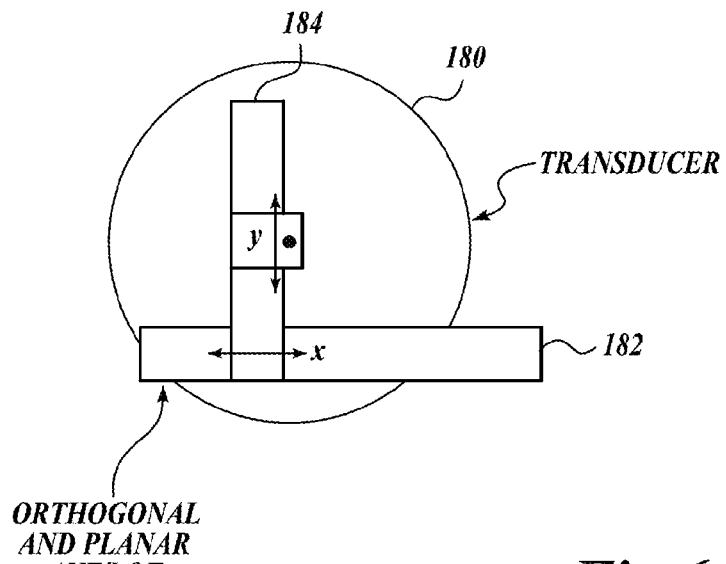
FIGS. 6C and 6D illustrate another mechanism for changing the depth and position of the focal zone.
Figure 6D:
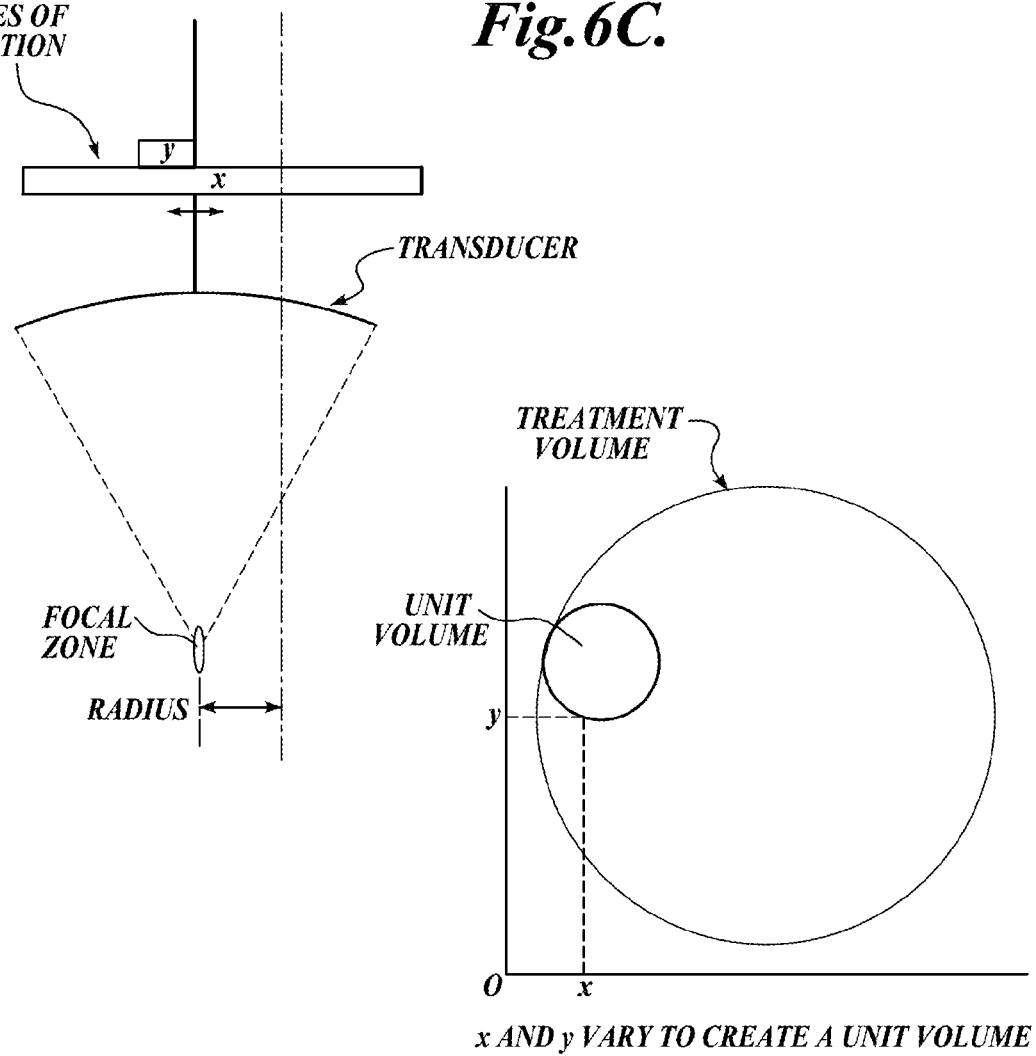

As will be appreciated, other mechanisms are possible to selectively position the focal zone of a HIFU transducer to create the elemental treatment volumes and treat the desired tissue volume. FIGS. 6C AND 6D illustrate another alternative embodiment where a transducer 180 is moved in two orthogonal directions (x,y) by a pair of linear actuators 182, 184. The linear actuators, which could be motors that drive a worm gear or other mechanisms, are computer controlled so that the position of the focal zone of the HIFU transducer 180 is moved as desired. A third motor or actuator (not shown) can be computer controlled to vary the height of the transducer 180 to change the depth of the focal zone.

Figure 7:
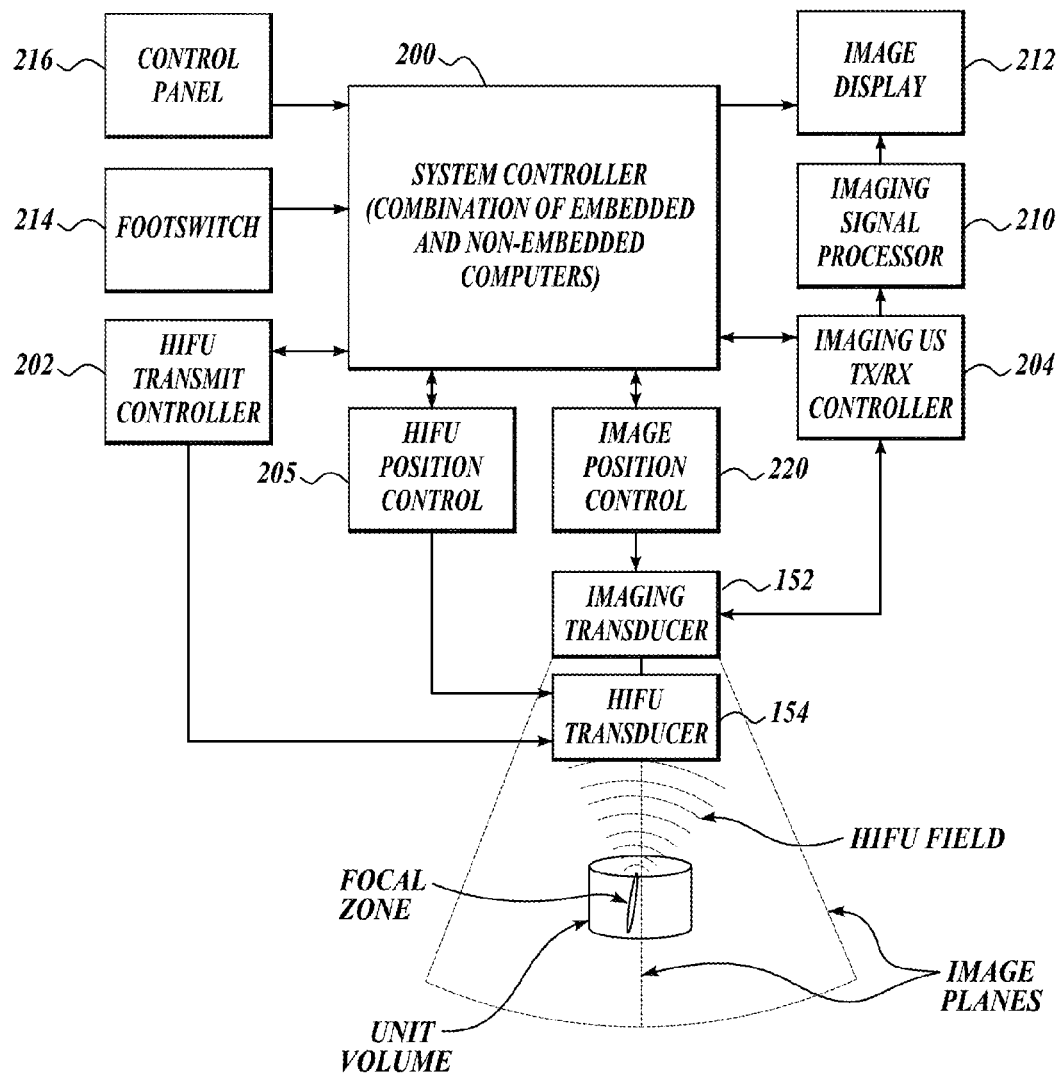
FIG. 7 illustrates a system for treating tissues with HIFU in accordance with an embodiment of the disclosed technology.

FIG. 7 illustrates a basic block diagram of a HIFU ultrasound treatment system in accordance with one embodiment of the disclosed technology. In this embodiment, a patient treatment device includes both a HIFU transducer 154 and an ultrasound imaging transducer 152. The transducers may be separate devices as shown in FIG. 6 or may be an integrated device with HIFU and imaging ultrasound elements located on the same transducer head. Controlling the operation of the imaging and HIFU transducers is a system controller 200 that may include one or more general purpose or special purpose programmed processors that are programmed to perform the functions described herein. The system controller 200 supplies control signals to a HIFU control unit 202 that selects the power of the HIFU signals to be provided by the HIFU transducer 154.

In one embodiment, the operating power level is selected by transmitting a number of test signals at different power levels and analyzing the echo signals created in response to the transmitted test signals. The operating power level for HIFU treatment is selected when a desired characteristic of an echo signal is observed, such as when a certain distribution of power at different fundamental and harmonic frequency components is detected within the echo signal. This particular embodiment for selecting the operating power level based on a pre-treatment acoustic assessment the spectral power distribution will be described in more detail subsequently. Further detail of possible methods of selecting and controlling the HIFU power can be found in U.S. patent application Ser. No. 12/537,217 filed Aug. 6, 2009 (U.S. Patent Publication No. 2010/0036292) and which is herein incorporated by reference.

The imaging transducer 152 is controlled by an imaging ultrasound controller 204 that includes conventional ultrasound components such as a transmit/receive switch, beamformer, RF amplifiers and signal processors. The output of the ultrasound controller 204 is fed to an ultrasound signal processor 210 that operates to produce ultrasound imaging signals for display on a video monitor 212 or other display. The image signals can also be stored on a computer readable media (DVD, video tape, etc.), printed by a printer or otherwise stored for later diagnosis or analysis.

A computer controlled steerer 205 (or position control) is controlled by the system controller 200 to create a number of elemental treatment volumes to treat a desired volume of tissue. In one embodiment, the computer controlled steerer 205 mechanically adjusts the angular orientation or x,y position of the HIFU transducer 154 and the depth of the focal zone to direct the HIFU energy at a desired location. In another embodiment, the computer controlled steerer 205 electronically adjusts the angular orientation or x,y position of the focal zone of the HIFU transducer 154 and the depth of the focal zone of the HIFU transducer 154 to create the elemental treatment volumes.

A footswitch 214 allows a physician or their assistant to selectively deliver HIFU energy to the patient in order to treat a tissue site. In addition, the physician can manually change the size and shape of the treatment volume and other functions of the system using one or more controls on a control panel 216.

In some embodiments, the system may include an image position control 220 that changes the orientation of the imaging transducer 152 so that the physician can view the desired target tissue volume to be treated at different angles or in different planes. The image position control be either mechanical or electronic and is controlled by the system controller 200.

The system shown in FIG. 7 does not require the use of temperature data or other feedback control to treat tissue. Because the temperature data or feedback control is not required, systems for detecting the data, such as an MRI machine are not required. This allows the system disclosed herein to be made small enough such that it can be used in a physician's office.

As indicated above, it has been determined that significant benefits can be obtained both in terms of a reduction in the time required to create a lesion and their uniformity if HIFU treatment signals are delivered at power levels where the treatment signal becomes non-linear in the tissue. In one embodiment mentioned above, a power level used to treat the tissue is selected based on the detected energy in one or more harmonics of the fundamental frequency. Another way of detecting the same effect is to measure the conversion of energy from the fundamental frequency of the treatment signal to the harmonics of the fundamental with changes in applied power and to use the measured conversion as a way to select a power level for the treatment signals.

Figure 10:
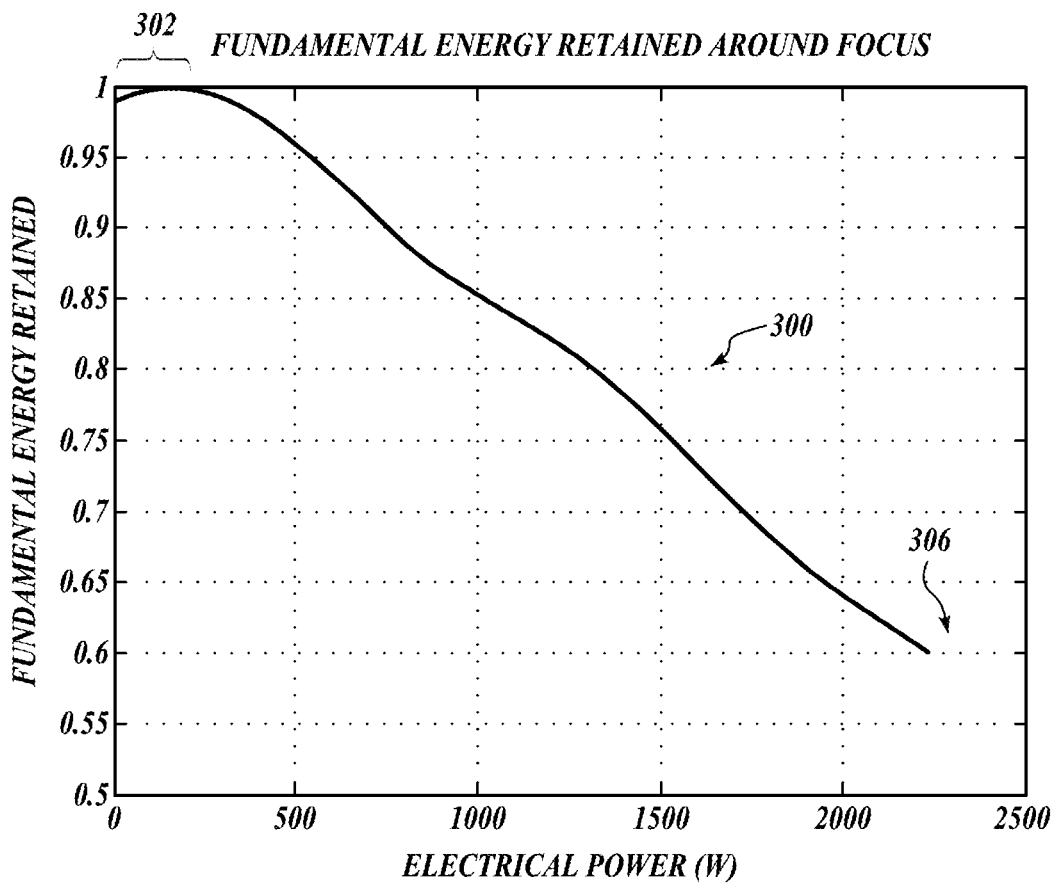
FIG. 10 illustrates a fundamental energy retained (FER) curve calculated in accordance with another aspect of the disclosed technology.

FIG. 10 shows a curve 300 that plots the amount of energy backscattered from the focal zone that is retained at the fundamental frequency of a HIFU treatment signal versus changes in electrical power delivered to the HIFU transducer. In this example, the curve reaches a normalized maximum of 1.0 at approximately 200 watts where substantially all the energy (100%) in a backscatter signal detected is contained at the fundamental frequency. However, as the electrical power delivered is increased, energy is converted from the fundamental frequency to harmonics of the fundamental frequency and the fundamental energy retained (FER) decreases. For example, in FIG. 10, at an applied power of 1500 W, the FER value of ~0.75 indicates that 75% of the focal signal remains at the fundamental frequency, while the other 25% has been converted into harmonic frequencies. As will be explained in further detail below, the FER curve 300 can be used to select the transmit power of the HIFU signals that will be used to treat the patient. It is possible, depending on tissue variance levels, that the FER curve is the only information needed to determine successful treatment.

In one embodiment, the FER curve 300 is computed by applying a number of test signals at different power levels to the treatment site, detecting received backscatter signals and determining how the frequency distribution of the energy in the backscatter signals differs from what the distribution would look like if the tissue were operating like a linear system. For example, for the linear system model, if a test signal of 500 watts of electrical power produces X energy at the fundamental frequency in the received backscatter signal, then 1000 watts of applied electrical power should produce 2× of energy at the fundamental frequency. Any variation from 2× deviates from a linear system and is therefore related to how much energy is being converted into energy at the harmonic frequencies.

In the FER curve 300, those points on the curve in a region 302 are associated with a signal to noise (S/N) ratio that may make their data unreliable. Similarly, those points on the curve in a region 306 are produced at power levels where cavitation is likely in the tissue. Because the tissue is changing state with cavitation, the backscatter signals received at this power level may also not be reliable to determine how much power is being converted to harmonics of the fundamental of the treatment signals.

Figure 11:
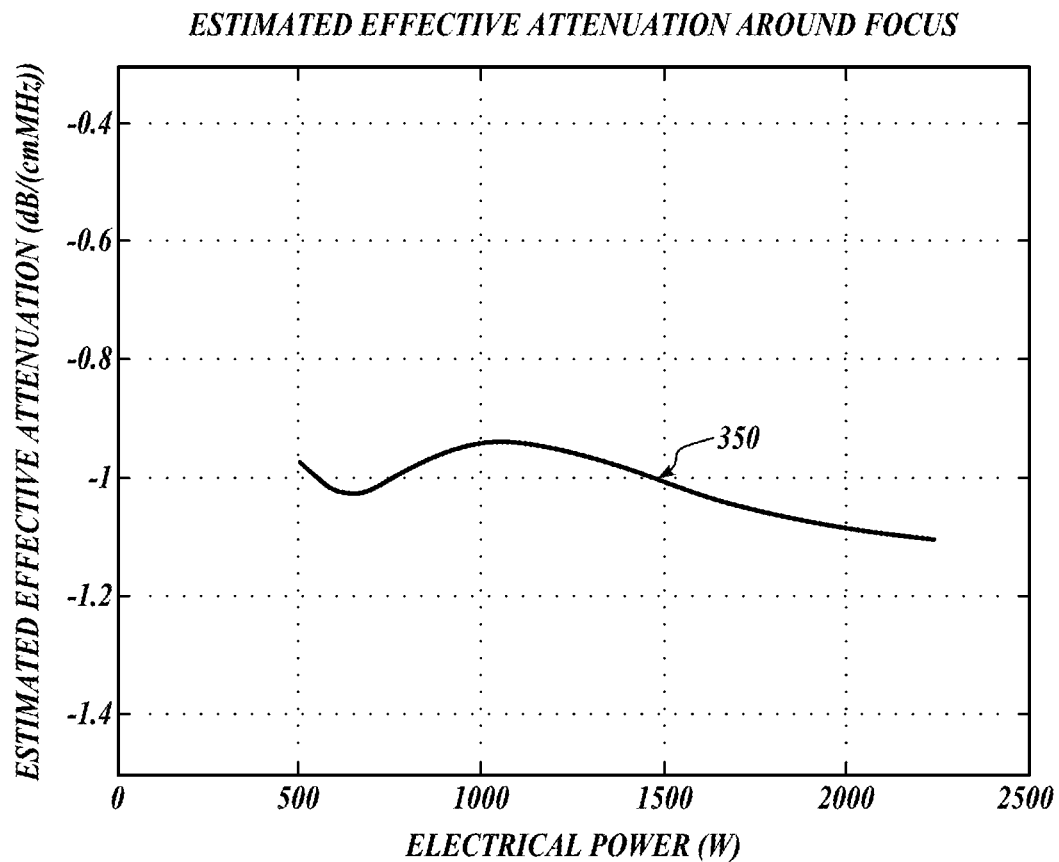
FIG. 11 shows a curve of an estimated attenuation of a HIFU signal in tissue around a focal zone of a HIFU transducer versus changes in applied power that is calculated in accordance with another aspect of the disclosed technology.

In order to determine the amount of power that should be applied to the patient to treat the tissue site, it may be necessary to determine how much of the applied power is actually delivered to the focal zone. However, in some cases, identifying the power level associated with the required FER value may be sufficient to determine the appropriate applied power. In cases where additional information is required, an estimation of the power actually delivered to the focal zone can be obtained by measuring the attenuation of the treatment signal between the HIFU transducer and the focal zone. FIG. 11 shows a curve 350 that plots the estimated attenuation between the HIFU transducer and the focal zone of the HIFU transducer versus changes in applied transmit power. In one embodiment described in further detail below, the FER curve 300 shown in FIG. 10 and the attenuation curve 350 shown in FIG. 11 are used to select a treatment power level.

Figure 12:
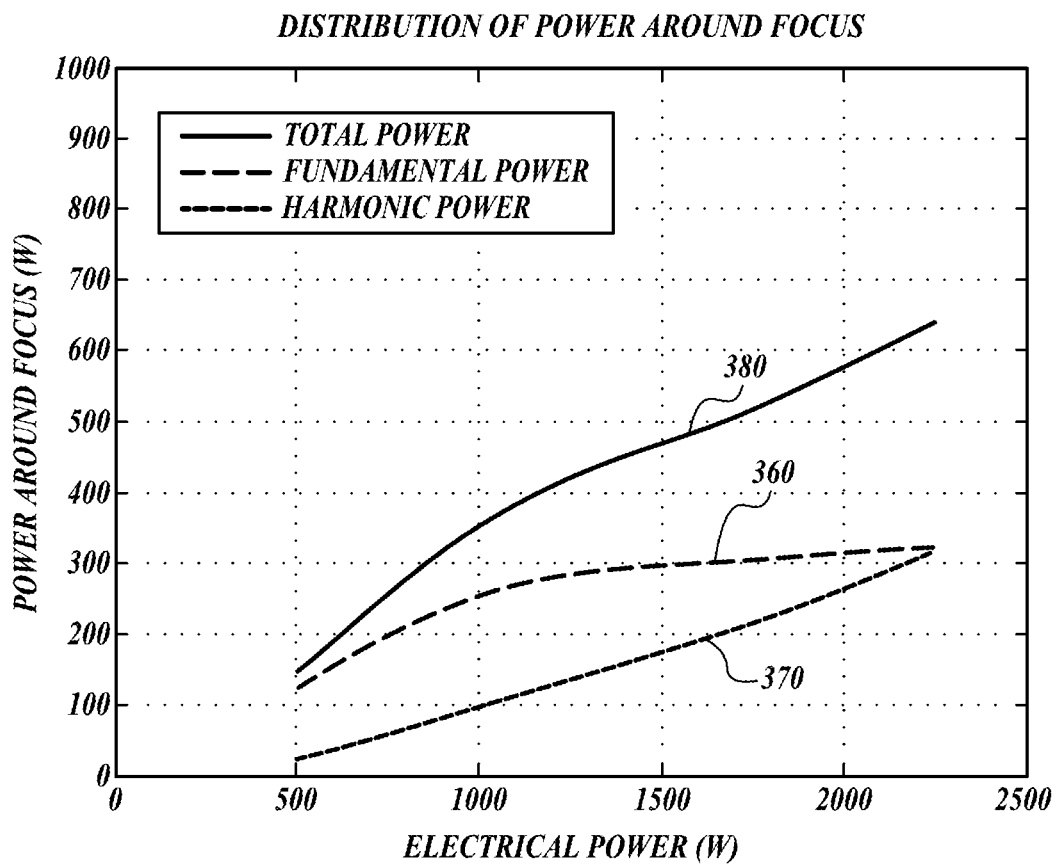
FIG. 12 illustrates a set of curves showing the total power delivered to a focal zone, the power retained at the fundamental frequency of the HIFU treatment signal and the power converted into harmonics that are calculated in accordance with another aspect of the disclosed technology.

FIG. 12 shows a curve 360 that plots the energy contained at the fundamental frequency around the focal zone versus changes in applied electrical power. A curve 370 plots changes in the energy contained in the harmonics of the fundamental frequency with changes in applied electrical power around the focal zone and a curve 380 plots the total power applied to the tissue around the focal zone (i.e. power at the fundamental and at the harmonics) versus changes in applied power.

In one embodiment, the curve 370 is used to select the treatment power of the HIFU signals. For example, empirically determined data obtained from animal trials or from other sources, may be used to select a desired power that should be delivered to the tissue at harmonics of the fundamental frequency. In trials on in-vivo porcine thighs, a level of 100-200 watts of harmonic power at the focal zone has been found to produce uniformly necrosed elemental treatment volumes with little collateral tissue damage, when used in conjunction with the acoustic waveform timing and motion profile parameters described herein. The curve 370 is used to determine what the input electrical power of the treatment signals should be in order to produce 100-200 watts of harmonic power. In the example curve shown, input power levels between 1000 and 1700 watts will produce between 100 and 200 watts of harmonic power. Therefore, by knowing the FER and attenuation curves for the tissue to be treated and what desired level of harmonic power should be delivered to the tissue, a determination can be made of what treatment power should be applied.

Figure 13:
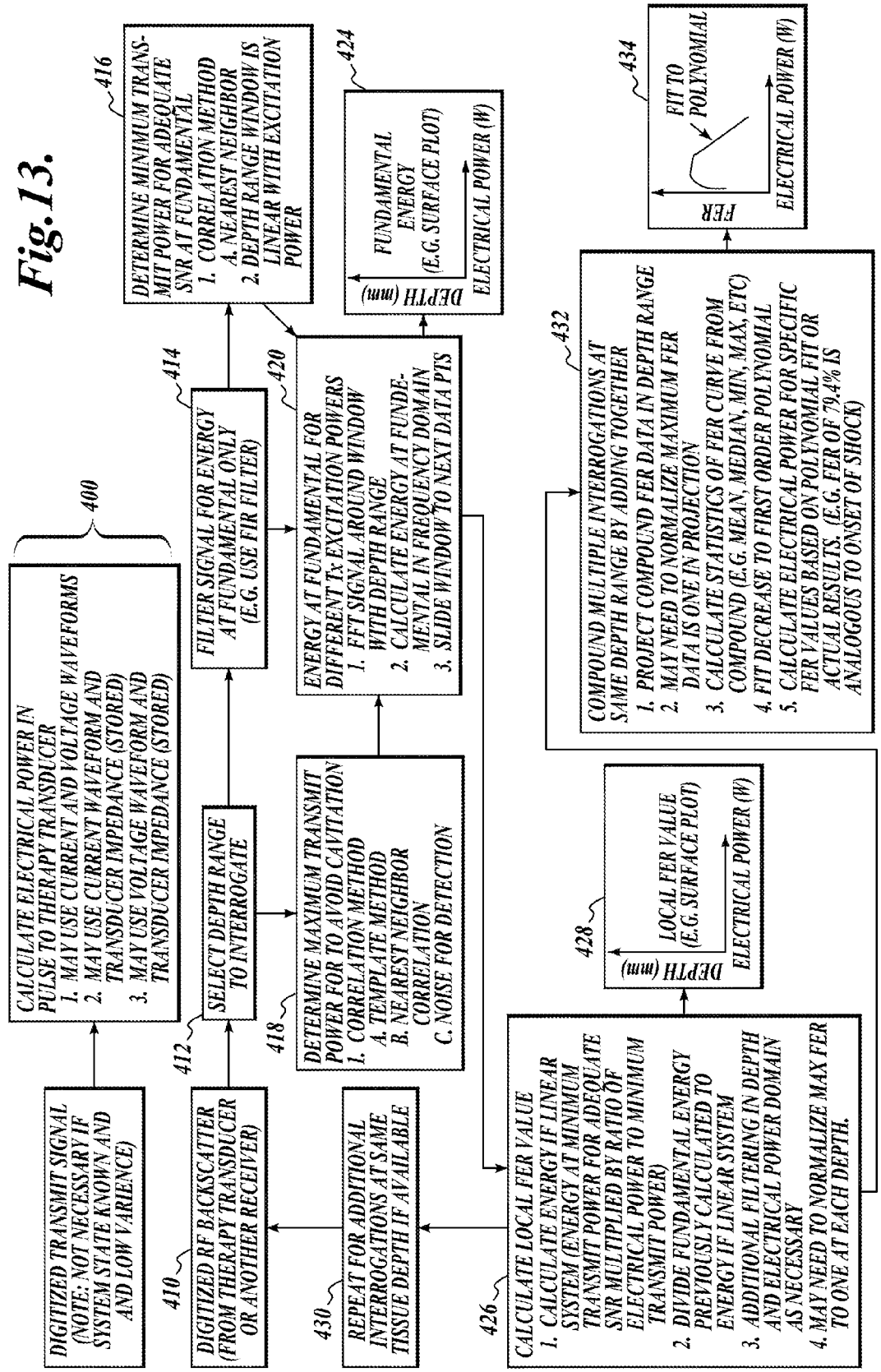
FIG. 13 is a flow diagram of a method of calculating how much power at a fundamental frequency of a treatment signal is converted into power at harmonics of the fundamental frequency in accordance with one embodiment of the disclosed technology.

Several methodologies for determining the FER and attenuation curves are now described. FIG. 13 is a signal processing flow diagram showing the steps used to compute a FER curve in accordance with one embodiment of the disclosed technology. At 400, the metric by which the HIFU output is measured (typically the transmit power level) is determined. For example, the transmit power level can be calculated from the current and voltage waveforms of the digitized transmit signals, or from either the current or voltage waveform of the transmit signals in conjunction with the impedance of the HIFU transducer. If the system state is known and stable, then the initial state can be reused when calculating an FER curve.

At 410, the RF backscatter signals from a number of test signals transmitted at different power levels are detected, digitized and stored in a memory or other computer readable media. At 412, a depth range to interrogate is selected that includes an area around the focal zone of the HIFU transducer. At 414, the RF backscatter signals are filtered to determine the energy at the fundamental frequency of the transmit signals.

At 416, the minimum transmit power needed to obtain backscatter signals with a good signal-to-noise (S/N) ratio at the fundamental frequency is determined. Such determination may be made by nearest neighbor correlation or by determining where the power detected in the window appears to be linear with changes in excitation power. A calculation is made at 418 to determine a transmit power level where cavitation in the tissue begins. Such a power level can be determined using, for example, a template method, nearest neighbor correlation or a noise floor calculation. Each of these techniques is considered known to those of ordinary skill in the art of ultrasound signal processing.

At 420, the energy at the fundamental frequency in a sliding window is determined for various transmit powers. The window size, which is typically determined by transmit pulse attributes, may be selected in response to user input, recalled from memory, or dynamically calculated. The energy in the window at the fundamental frequency is determined and the window is then moved to the next set of data points. The result is a surface plot 424 of the energy at the fundamental frequency at various depths in the tissue versus changes in transmit power.

At 426, the amount of fundamental energy retained (FER) in the backscatter signal for each depth in the depth range is determined. In one embodiment, the energy at the fundamental contained in the backscatter signal for a particular depth is compared with the energy that would be expected if the tissue were operating as a linear system. The expected energy $E_{exp}$ may be determined by multiplying the energy $E_0$ at the fundamental detected at a lower power $P_L$ that is sufficient to produce signals with a good signal to noise ratio by the quotient of the transmit power in question $P_H$ divided by $P_L$. The differences between the energy actually detected at the fundamental and the expected energy $E_{exp}$ is used to produce a surface plot 428 of the local FER values versus depth and applied power.

The process described above, may be repeated for different interrogation angles or positions around the focal zone at 430.

At 432, the results obtained for the local FER values are compounded (such as by averaging the value) for each angle interrogated (if any). The compounded results are fit to a polynomial (which may be first order such as a line) or other mathematically defined function. In one embodiment, the FER curve is normalized to one, such that all values in the FER curve are less than one for depths and power levels where energy is being converted from the fundamental to the harmonics of the fundamental.

As will be appreciated, there are other techniques for producing the FER curve. For example, the filtering at 414 can be done with a digital FIR (finite impulse response) filter and an FFT (fast Fourier transform) can be performed at 420 to determine the amount of energy in the received backscatter signals at the fundamental frequency. Similarly, the signal processing can be performed at baseband by multiplying the backscatter signal by the carrier signal and applying a low pass filter such that the amplitude of the remaining signal is indicative of the energy contained at the fundamental.

To select the treatment power in accordance with this embodiment, it is also necessary to know how much power applied at the tissue surface is actually delivered at the focal zone. To determine this, a computer, such as the system controller 200, is programmed to make an estimation of what the attenuation is in the tissue path from the transducer to the tissue site to be treated. Attenuation values can be recalled from a memory that stores values based on prior experiments or from literature studies for well-known tissue types. However because each patient's physiology is different, the attenuation can also be estimated based on the response of the tissue to one or more test signals.

In the embodiment shown in FIG. 14, the attenuation of the HIFU signal between the HIFU transducer and the target treatment site is determined by applying a number of test signals at different power levels. At 502, the actual power of the signals applied by the HIFU transducer is determined either from previously determined measurements or from the digitized current and voltage waveforms applied to the transducer. Alternatively, if the impedance of the transducer is known, the current or voltage waveforms can be used to calculate the power.

In response to a number of test signals being transmitted at different power levels, a number of RF backscatter signals are detected at 504. In one embodiment, such signals are detected with a wide bandwidth receiver (e.g. the imaging transducer 152) that can detect signals at for example, the $2^{nd}$-$4^{th}$ harmonics of the transmit signal (other harmonics may be used if available).

At 512, a depth range is selected for which the attenuation is to be measured. The depth range will typically include the focal zone of the transducer. At 514, a window of data in each of the backscatter signals is selected that includes the selected depth range. At 516, the system controller 200 or other computer performs an FFT or some other frequency analysis to determine how much energy is present in each of the $2^{nd}$-$4^{th}$ or higher harmonics in the backscatter signals. The energy in the harmonics is then corrected for the response of the detection system due to, for example, roll-off in the pre-amplifiers or the frequency response of the detecting transducer. At 520 the delivered power for which the RF backscatter signals have a good signal-to-noise (S/N) ratio at the harmonics is determined. This power will likely be greater than that required to produce signals with a good S/N ratio at the fundamental frequency. At 518, the power level at which cavitation begins is also determined in the manner described above. A surface plot of the energy at different frequencies versus changes in applied electrical power is calculated at 524. The energy at each harmonic versus applied electrical power is calculated at 526. The steps 510-526 can be repeated for different interrogation points at 528. In one embodiment, measurements are made at 10 points surrounding the desired treatment site.

Once the energy of the harmonics versus changes in applied electrical power have been determined for each of the interrogation points, the results are compounded such as by averaging at 530.

In one embodiment of the disclosed technology, an assumption is made that harmonics are emanating from the vicinity of the focal zone of the HIFU transducer and are created predominantly as result of the nonlinear propagation of the applied HIFU signal. Therefore it is also assumed that signals at the harmonic frequencies are only attenuated on a one-way path from the focal zone back to the detection transducer. In general it is known that signal amplitudes for harmonics generated in tissue should experience a roll-off. For example, if the amount of harmonics has saturated, the roll-off follows a $1/n$ behavior (where n indicates the $n^{th}$ harmonic). This roll-off should be corrected for and can be determined by the FER value. Because the detected energies of the harmonics have already been corrected for the frequency response of the receiving electronics and detecting transducer, once the harmonic levels have been corrected for the roll off present, any difference in amplitude between the harmonic peaks may be attributed to attenuation. At 532, the energy level of each harmonic at a particular input power level is determined and fitted with a polynomial (or a line). The slope of the polynomial divided by the total length of the tissue path at the point where the signal is measured gives the attenuation of the HIFU signals in units of dB/MHz-cm. This calculation is performed for other applied input powers between the minimum required for good signal-to-noise ratio and the power level at which cavitation begins. The result is an attenuation curve that plots attenuation versus applied input power.

In some situations, it may be desirable to determine a local attenuation value such as in a fibroid itself. As shown in steps 544, the HIFU transducer may be moved with respect to the tissue or its focal zone changed and the new attenuation curve determined in the manner described above. The local attenuation at any given input power is therefore equal to the difference of the attenuation values at each depth, multiplied by their respective depths, divided by the difference in depths.

Once the FER curve and the attenuation curve of the tissue are known, an appropriate input power for treatment is determined by multiplying the input power by the attenuation curve 350 at a number of power levels between the minimum needed for a good S/N ratio and the power level where cavitation begins. As shown in FIG. 12, scaling the input power by the attenuation curve 350 (FIG. 11) results in the curve 380 shown in FIG. 12. From the curve 380, the curve 360 is calculated by scaling the curve 380 by the FER curve 300. Finally, the power in the harmonics curve 370 can be calculated by subtracting the curve 360 from the curve 380. From the curve 370 the appropriate input power necessary to achieve the desired harmonic power in the tissue can be determined as indicated above.

As will be appreciated, the power of the treatment signals used to treat the tissue can also be predetermined and recalled from stored memory based on a measured characteristic of the tissue in question. If the local attenuation of the tissue is known, a FER curve based on previously performed studies can be used to predict how much energy should be applied to achieve a desired harmonic power at the treatment site. Alternatively, if the FER curve is determined for the tissue in question, a treatment power can be selected based on previously performed studies. Another option relying on predetermined empirical treatment set points is to measure the height of any part of the tissue path that is effectively non-attenuative (e.g., urine contained within the bladder) and reduce the empirically-determined power value known for that tissue depth by the appropriate amount to account for the non-attenuative portion. For example, if the tissue path for a 10 cm treatment depth contains a 2-cm segment composed of urine in the bladder, then the empirically-determined power value for a 8-cm treatment depth can be applied instead as a first-order approximation of the appropriate HIFU output level.

With the foregoing description, various embodiments of the disclosure may be implemented, including but not limited to the following examples.

In at least one example, a system for treating uterine fibroids or other uterine tissue may comprise a hand-held or hand-guided HIFU applicator with a movable transducer focal zone that is configured to deliver HIFU treatment signals to a treatment site in a uterine fibroid or other uterine tissue; an imaging transducer that produces imaging signals representative of the uterine fibroids or other uterine tissue; and a processor programmed to determine a pattern in which to apply HIFU around the periphery of a fibroid or other targeted volume of uterine tissue and to control the position of the focal zone of the HIFU transducer to apply HIFU energy in this pattern.

In various embodiments, the pattern in which HIFU is applied consists of a number of elemental treatment volumes created around the periphery of the fibroid or other targeted volume of uterine tissue. Each elemental treatment volume may have a size selected such that an interior region is treated by indirect heating as the treatment energy is repeatedly applied to a perimeter of the elemental treatment volume. Furthermore, the processor may be programmed to control the position the focal zone of the HIFU transducer in a pattern to create a number of elemental treatment volumes within an interior of the uterine fibroid or the targeted volume of uterine tissue.

In various embodiments, the HIFU treatment signals are transmitted at a power sufficient to convert a substantial portion of the power at a fundamental frequency of the therapeutic HIFU signals to power in the harmonics of the fundamental frequency at the treatment site. The processor may be programmed to determine a power level for the HIFU treatment signals such that a substantial portion of the power at a fundamental frequency of the therapeutic HIFU signals is converted to power in the harmonics of the fundamental frequency at the treatment site based on a number of test signals transmitted at different power levels. The elemental treatment volume may be cylindrical and have a diameter approximately equal to a length of the focal zone. The processor may be programmed to: control a mechanical linkage that adjusts the position of the HIFU transducer to move the focal zone; control an electronic beam steerer to move the focal zone; automatically detect the boundaries of the uterine fibroid or other volume of uterine tissue to be treated; and/or receive input from a user that is indicative of the boundaries of the uterine fibroid or other volume of uterine tissue to be treated.

In another example, a system for thermally necrosing a uterine fibroid or other uterine tissue with high intensity focused ultrasound (HIFU) may comprise a hand-held or hand-guided HIFU applicator with a movable transducer focal zone that is configured to deliver therapeutic HIFU signals having a fundamental frequency to the treatment site; a transmit controller configured to supply driving signals to the HIFU transducer such the transducer produces therapeutic HIFU signals at a power sufficient to convert a substantial portion of the power at a fundamental frequency of the therapeutic HIFU signals to power in the harmonics of the fundamental frequency at the treatment site; and a position controller that is configured to position the focal zone of the HIFU transducer in the uterine fibroid or other uterine tissue to create one or more elemental treatment volumes without temperature feedback.

In various embodiments, each elemental treatment volume may be a cylinder having a diameter substantially equal to a length of the focal zone. The power of the HIFU treatment signals is selected that the HIFU treatment signals reach or exceed the onset of shock at the treatment site.

In yet another example, a system for thermally necrosing tissue at a treatment site with high intensity focused ultrasound (HIFU) may comprise a HIFU transducer with a movable focal zone that is configured to deliver therapeutic HIFU signals having a fundamental frequency to the tissue at the treatment site; a transmit controller configured to supply driving signals to the HIFU transducer such that the transducer produces therapeutic HIFU signals at a power sufficient to convert a substantial portion of the power at a fundamental frequency of the therapeutic HIFU signals to power in the harmonics of the fundamental frequency at the treatment site; and a position controller that is configured to position the focal zone of the HIFU transducer in the tissue to create one or more elemental treatment volumes in the presence of bubbles.

In still another example, a system for treating uterine fibroids or other uterine tissue may comprising a hand-held or hand-guided HIFU applicator with a movable transducer focal zone that is configured to deliver HIFU treatment signals to a treatment site in a uterine fibroid or other uterine tissue; an imaging transducer that produces imaging signals representative of the treatment site; a processor programmed to determine a pattern in which to apply HIFU to a fibroid or other targeted volume of uterine tissue; and a position controller that selectively controls the position of the focal zone of the HIFU transducer to apply HIFU energy in the determined pattern such that a fibroid or other volume of uterine tissue up to 5 cm in diameter can be effectively treated in under 10 minutes.

While illustrative embodiments have been illustrated and described, it will be appreciated that various changes can be made therein without departing from the scope of the invention. For example, although the energy source used to create the ablated shell is HIFU in the disclosed embodiments, other energy sources could be used such as radiation, lasers, RF, microwaves, cryoablation, etc. Some of these energy sources are minimally invasive such that they must be delivered to the tissue volume with a catheter, endoscope, or the like. Applying energy from these energy sources ablates the perimeter of the tissue volume to create an ablated shell. In another embodiment, the HIFU transducer may be insertable in to the body such as transvaginally or rectally. If the tissue volumes to be treated can be seen from the location of the HIFU transducer, then images of the tissue can be obtained with image sensors other than ultrasound image sensors. In some embodiments, the imaging of the desired treatment volume may be done with another type of imaging modality such as MRI, x-ray, infrared, or the like in a manner that allows a physician to confirm that the HIFU is being delivered to the area of desired target tissue volume. Therefore, the scope of the invention is to be determined from the following claims and equivalents thereof.

The embodiments of the invention in which an exclusive property or privilege is claimed are defined as follows:

1. A system for treating a volume of tissue at a treatment site with high intensity focused ultrasound (HIFU), the system comprising:
   a HIFU transducer that delivers HIFU treatment signals to tissue at a movable focal zone within the treatment site; and
   one or more processors programmed to control a supply of driving signals to the HIFU transducer that cause the HIFU transducer to deliver the HIFU treatment signals to the treatment site at a selected power, and further to control positioning of the focal zone of the HIFU transducer such that the HIFU treatment signals create a plurality of elemental treatment volumes at a periphery of the volume of tissue,
   wherein the elemental treatment volumes are smaller than the volume of tissue at the treatment site and are distributed both vertically and horizontally relative to each other at the periphery of the volume of tissue,
   wherein HIFU energy is distributed in multiple doses in a trajectory over or along a perimeter of each elemental treatment volume, with repeated passes of the focal zone of the HIFU transducer in the same trajectory over or along the perimeter of each elemental treatment volume, and
   wherein the horizontal and vertical distribution of the elemental treatment volumes relative to each other at the periphery of the volume of tissue produces a shell of treated tissue around an interior space of the volume of tissue.

2. The system of claim 1, wherein the elemental treatment volumes are cylindrical elemental treatment volumes created by directing the focal zone around the perimeter of each elemental treatment volume.

3. The system of claim 2, wherein the focal zone is continuously moved around the perimeter of an elemental treatment volume while the HIFU transducer continually delivers the HIFU treatment signals.

4. The system of claim 2, wherein the focal zone is moved to discrete positions around the perimeter of an elemental treatment volume while the HIFU transducer delivers the HIFU treatment signals in pulses.

5. The system of claim 1, wherein at least one elemental treatment volume has a center area that is not directly exposed or is minimally exposed to the focal zone of the HIFU treatment signals such that heat is conducted to the center area as the focal zone moves over or along the perimeter of the elemental treatment volume.

6. The system of claim 5, wherein the elemental treatment volume is sized such that, once treated, the elemental treatment volume has a cross section that is treated through the center area of the elemental treatment volume.

7. The system of claim 5, wherein the elemental treatment volume is sized such that, once treated, heat conduction does not fully occur through the center area while the perimeter of the elemental treatment volume is ablated.

8. The system of claim 1, wherein the HIFU treatment signals distribute HIFU energy in segments over along the perimeter of an elemental treatment volume by passing the focal zone of the HIFU transducer in the same trajectory over or along the length of each segment multiple times.

9. The system of claim 8, wherein each segment is shaped as an arc created side-by-side to treat the perimeter of the elemental treatment volume.

10. The system of claim 1, further comprising a mechanical wobbler that steers the focal zone of the HIFU treatment signals over or along the perimeter of each elemental treatment volume at a rate that confines heat conduction within a center of each elemental treatment volume as the elemental treatment volumes are being created.

11. The system of claim 1, further comprising an electronic beam steerer that steers the focal zone of the HIFU treatment signals over or along the perimeter of each elemental treatment volume at a rate that confines heat conduction within a center of each elemental treatment volume as the elemental treatment volumes are being created.

12. The system of claim 1, wherein the HIFU treatment signals delivered by the HIFU transducer comprise substantially non-linear pulsed waveforms of HIFU energy that are applied to the perimeter of each elemental treatment volume.

13. The system of claim 12, wherein the pulsed waveforms of HIFU energy are nonlinear such that an originally sinusoidal characteristic of the waveforms is distorted by the time the HIFU energy reaches the focal zone and energy in a fundamental acoustic frequency of the waveforms is converted to higher harmonic acoustic frequencies.

14. The system of claim 13, wherein the power of the HIFU treatment signals is selected to obtain a desired nonlinearity of the waveforms and conversion of HIFU energy from the fundamental acoustic frequency to the higher harmonic acoustic frequencies.

15. The system of claim 1, wherein the elemental treatment volumes are horizontally and vertically distributed in annular patterns having increasing internal diameter that extend from a distal end of the tissue at the treatment site to an annular pattern of maximum diameter, at which the annular patterns have decreasing internal diameter to a proximal end of the volume of tissue being treated.

16. The system of claim 1, wherein some or all of the tissue within a center of the shell of treated tissue necroses due to heat conduction from when the shell is being produced.

17. The system of claim 1, wherein the shell includes one or more gaps between elemental treatment volumes depending on the size of the elemental treatment volumes, the horizontal and vertical distribution of the elemental treatment volumes, a thermal conductivity of the tissue at the treatment site, and a HIFU energy absorption characteristic of the tissue at the treatment site.

18. A system for treating a volume of tissue at a treatment site with high intensity focused ultrasound (HIFU), the system comprising:
   a HIFU transducer that delivers HIFU treatment signals to tissue at a movable focal zone within the treatment site; and
   one or more processors programmed to control a supply of driving signals to the HIFU transducer that cause the HIFU transducer to deliver the HIFU treatment signals to the treatment site at a selected power, and further to control positioning of the focal zone of the HIFU transducer such that the HIFU treatment signals create a plurality of toroids having varying internal diameter at a periphery of the volume of tissue,
   wherein the toroids are smaller than the volume of tissue at the treatment site and are distributed vertically relative to each other in a stacked series of toroids at the periphery of the volume of tissue, wherein the HIFU treatment signals distribute HIFU energy in multiple doses in a trajectory over or along a perimeter of each toroid, with repeated passes of the focal zone of the HIFU transducer in the same trajectory over or along the perimeter of each toroid, and wherein the stacked series of toroids produces a shell of treated tissue around an interior space of the volume of tissue.

19. The system of claim 18, wherein a first toroid of minimal internal diameter is created at a distal end of the tissue at the treatment site and additional toroids of increasing diameter are created proximally to the first toroid to a toroid having a maximum internal diameter, at which additional toroids of decreasing internal diameter are created until the shell is closed with a second toroid of minimal internal diameter.

20. A system for treating a volume of tissue at a treatment site with high intensity focused ultrasound (HIFU), the system comprising:

a HIFU transducer that delivers HIFU treatment signals to tissue at a movable focal zone within the treatment site; and one or more processors programmed to control a supply of driving signals to the HIFU transducer that cause the HIFU transducer to deliver the HIFU treatment signals to the treatment site at a selected power, and further to control positioning of the focal zone of the HIFU transducer such that the HIFU treatment signals create a spiral of treated tissue at a periphery of the volume of tissue, wherein the spiral of treated tissue is smaller than the volume of tissue at the treatment site and is distributed around the volume of tissue at the periphery of the volume of tissue, wherein the spiral has a minimum diameter at a distal end of the tissue at the treatment site, and subsequent loops of the spiral have a diameter that expands to a loop of maximum diameter, at which the diameter of further subsequent loops of the spiral decreases to a proximal end of the volume of tissue, and wherein the HIFU treatment signals distribute HIFU energy in a spiral trajectory over or along the periphery of the volume of tissue such that the adjacent loops of the spiral produces a shell of treated tissue around an interior space of the volume of tissue.

* * * * *